US012775108B2

(12) United States Patent
Yu

(10) Patent No.: US 12,775,108 B2
(45) Date of Patent: Oct. 27, 2026

(54) DETECTOR SYSTEMS FOR IMAGING

(71) Applicant: SHANGHAI UNITED IMAGING HEALTHCARE CO., LTD., Shanghai (CN)

(72) Inventor: Jingyi Yu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 181 days.

(21) Appl. No.: 18/661,698

(22) Filed: May 12, 2024

(65) Prior Publication Data

US 2024/0302546 A1 Sep. 12, 2024

Related U.S. Application Data

(63) Continuation of application No. PCT/CN2021/132789, filed on Nov. 24, 2021.

(51) Int. Cl.
*G01T 1/24* (2006.01)
*A61B 6/42* (2024.01)

(52) U.S. Cl.
CPC ............ *G01T 1/241* (2013.01); *A61B 6/4208* (2013.01); *A61B 6/4266* (2013.01)

(58) Field of Classification Search
CPC ....... G01T 1/241; G01T 1/244; A61B 6/4208; A61B 6/4266; A61B 6/4291; A61B 6/035; A61B 6/4233; G01N 23/04
See application file for complete search history.

(56) References Cited

U.S. PATENT DOCUMENTS 3,593,067 A 7/1971 Flynn
7,355,185 B2 4/2008 Yasuda et al.
(Continued)

FOREIGN PATENT DOCUMENTS

JP 2009259859 A 11/2009
JP 2017146244 A 8/2017
RU 2306633 C1 9/2007

OTHER PUBLICATIONS

International Search Report in PCT/CN2021/132789 mailed on Jul. 27, 2022, 6 pages.
(Continued)

*Primary Examiner* — Kiho Kim
(74) *Attorney, Agent, or Firm* — METIS IP LLC

(57) ABSTRACT

Detector systems are provided. The detector system may include a plurality of edge-on detector modules. Each edge-on detector module may include: a silicon substrate including a front side corresponding to a first side of the each edge-on detector module and a rear side corresponding to a second side of the each edge-on detector module; a plurality of detection elements disposed on the front side of the silicon substrate; a backside electrode disposed on the rear side of the silicon substrate; and/or an anti-scatter structure disposed on at least one of the first side or the second side of the each edge-on detector module, the anti-scatter structure being configured to prevent or reduce scattering of photons emitted into the silicon substrate. The silicon substrate, the plurality of detection elements, the backside electrode, and/or the anti-scatter structure may be configured as an integral piece.

20 Claims, 10 Drawing Sheets

(56) References Cited

U.S. PATENT DOCUMENTS

| | | | |
|---|---|---|---|
| 7,727,796 | B2 | 6/2010 | Sipilae et al. |
| 10,126,437 | B1 | 11/2018 | Danielsson et al. |
| 10,191,162 | B2 | 1/2019 | Danielsson et al. |
| 10,386,506 | B2 | 8/2019 | Danielsson et al. |
| 10,656,290 | B2 | 5/2020 | Wieczorek et al. |
| 11,086,032 | B1 | 8/2021 | Hjärn et al. |
| 2007/0007459 | A1 | 1/2007 | Shibayama et al. |
| 2007/0090477 | A1 | 4/2007 | Shibayama |
| 2009/0274266 | A1 | 11/2009 | Sun et al. |
| 2010/0204942 | A1 | 8/2010 | Danielsson et al. |
| 2012/0217407 | A1 | 8/2012 | Iwakiri et al. |
| 2016/0157791 | A1 | 6/2016 | Shizukuishi |
| 2016/0296184 | A1 | 10/2016 | Rodrigues et al. |
| 2017/0018588 | A1 | 1/2017 | Karim et al. |
| 2017/0265822 | A1 | 9/2017 | Du |
| 2018/0042562 | A1 | 2/2018 | Danielsson et al. |
| 2018/0268952 | A1* | 9/2018 | Glatz ..................... G21K 1/025 |
| 2018/0321394 | A1* | 11/2018 | Danielsson ............. G01T 1/241 |
| 2019/0383955 | A1 | 12/2019 | Hjärn et al. |
| 2020/0150291 | A1 | 5/2020 | Cao et al. |
| 2020/0395496 | A1 | 12/2020 | Yamada et al. |

OTHER PUBLICATIONS

Written Opinion in PCT/CN2021/132789 mailed on Jul. 27, 2022, 4 pages.

The Extended European Search Report in European Application No. 21965071.0 mailed on Apr. 24, 2024, 10 pages.

X. Liu et al., Count Rate Performance of a Silicon-Strip Detector for Photon-Counting Spectral CT, Nuclear Instruments and Methods in Physics Research A, 827: 102-106, 2016.

* cited by examiner

400A

400B

400C

DETECTOR SYSTEMS FOR IMAGING

CROSS-REFERENCE TO RELATED APPLICATIONS

This application is a Continuation of International Application No. PCT/CN2021/132789, filed on Nov. 24, 2021, the contents of which are hereby incorporated by reference.

TECHNICAL FIELD

The present disclosure generally relates to imaging technology, and more particularly, relates to systems and methods for detector systems for imaging.

BACKGROUND

Imaging (e.g., X-ray imaging) is a common medical imaging technique. Semiconductor-based detector module (s) can be used in an X-ray imaging system to detect X-rays passing through an object (e.g., a patient). The semiconductor-based detector module(s) may include a plurality of edge-on silicon detectors. In X-rays detection(s), photon interaction(s) may take place in silicon substrate(s) of the edge-on silicon detector(s), which may result in scattering of photons emitted into the silicon substrate, thereby affecting signal(s) detected by the edge-on silicon detector(s). Therefore, it is desirable to provide detector systems to effectively prevent or reduce scattering of photons emitted into the silicon substrate.

SUMMARY

In one aspect of the present disclosure, a detector system is provided. The detector system may include a plurality of edge-on detector modules. Each edge-on detector module may include: a silicon substrate including a front side corresponding to a first side of the each edge-on detector module and a rear side corresponding to a second side of the each edge-on detector module; a plurality of detection elements disposed on the front side of the silicon substrate; a backside electrode disposed on the rear side of the silicon substrate; and/or an anti-scatter structure disposed on at least one of the first side or the second side of the each edge-on detector module, the anti-scatter structure being configured to prevent or reduce scattering of photons emitted into the silicon substrate. The silicon substrate, the plurality of detection elements, the backside electrode, and/or the anti-scatter structure may be configured as an integral piece.

In another aspect of the present disclosure, a detector system is provided. The detector system may include at least one edge-on detector module. The at least one edge-on detector module may include: a semiconductor substrate configured to transform photons into electrical signals; a plurality of detection elements and a backside electrode that are configured to collect the electrical signals; and/or an anti-scatter structure configured to reduce or prevent scattering of the photons at least between the at least one edge-on detector module and one or more adjacent edge-on detector modules. The silicon substrate, the plurality of detection elements, the backside electrode, and/or the anti-scatter structure may be configured as an integral piece.

In a further aspect of the present disclosure, an imaging device is provided. The imaging device may include at least one edge-on detector module. The at least one edge-on detector module may include: a silicon substrate including a front side corresponding to a first side of the each edge-on detector module and a rear side corresponding to a second side of the each edge-on detector module; a plurality of detection elements disposed on the front side of the silicon substrate; a backside electrode disposed on the rear side of the silicon substrate; and/or an anti-scatter structure disposed on at least one of the first side or the second side of the each edge-on detector module, the anti-scatter structure being configured to prevent or reduce scattering of photons emitted into the silicon substrate. The silicon substrate, the plurality of detection elements, the backside electrode, and/or the anti-scatter structure may be configured as an integral piece.

In some embodiments, the plurality of edge-on detector modules may be positioned next to each other and configured to detect X-rays; each edge-on detector module may include an incidence edge adapted to be oriented towards an X-ray source that generates the X-rays; the front side and/or the rear side of the silicon substrate may be substantially parallel to an incidence direction of the X-rays; or the scattering may include at least Compton scattering.

In some embodiments, the anti-scatter structure may be made of a material including a high atomic number material.

In some embodiments, the plurality of detection elements may include at least one of an aluminum electrode or a tungsten electrode.

In some embodiments, the anti-scatter structure may be disposed on the first side of the each edge-on detector module; the anti-scatter structure may include a plurality of anti-scatter units; and/or each anti-scatter unit of the plurality of anti-scatter units may correspond to one of the plurality of detection elements.

In some embodiments, at least one of the plurality of anti-scatter units may be disposed on a corresponding detection element.

In some embodiments, the at least one of the plurality of anti-scatter units and the corresponding detection element of the plurality of detection elements may have a same shape and/or area size in a plane parallel to the front side of the silicon substrate.

In some embodiments, the at least one of the plurality of anti-scatter units may be disposed on the corresponding detection element through at least one of evaporation or sputtering.

In some embodiments, at least one of the plurality of anti-scatter units may be disposed on the front side of the silicon substrate and electrically coupled to a corresponding detection element; and/or the at least one of the plurality of anti-scatter units may be configured as a lead-out line of the corresponding detection element.

In some embodiments, the at least one of the plurality of anti-scatter units may include two anti-scatter units insulated from each other.

In some embodiments, the each edge-on detector module may further include an insulating layer between each of the at least one of the plurality of anti-scatter units and the front side of the silicon substrate.

In some embodiments, at least one of the plurality of anti-scatter units may be disposed on a corresponding detection element; the at least one of the plurality of anti-scatter units may be electrically coupled to the corresponding detection element via a conducting material filled in a through hole of the at least one of the plurality of anti-scatter units; the at least one of the plurality of anti-scatter units may completely shield the corresponding detection element; and/or a size of the at least one of the plurality of anti-scatter units may be greater than a size of the corresponding detection element in a plane parallel to the front side of the silicon substrate.

In some embodiments, the at least one of the plurality of anti-scatter units may include two anti-scatter units insulated from each other.

In some embodiments, the at least one of the plurality of anti-scatter units may enclose the corresponding detection element.

In some embodiments, the plurality of anti-scatter units may have a same thickness along a direction perpendicular to the silicon substrate.

In some embodiments, the plurality of anti-scatter units may have different thicknesses along a direction perpendicular to the silicon substrate, and a thickness of an anti-scatter unit of the plurality of anti-scatter units may be related to a distance between the anti-scatter unit and a source that emits the photons.

In some embodiments, the detector system may further include an insulating layer disposed between the anti-scatter structure and the silicon substrate.

In some embodiments, a thickness of at least one of the plurality of anti-scatter units along a direction perpendicular to the silicon substrate may be within a range from 10 μm to 1000 μm.

In some embodiments, the anti-scatter structure and the plurality of detection elements may be made of a same material, and a thickness of the material may be greater than a second threshold; or the plurality of detection elements function as the anti-scatter structure, and a thickness of each of the plurality of detection elements may be greater than the second threshold.

In some embodiments, the material may include tungsten, and the second threshold may be 10 μm.

In some embodiments, the plurality of detection elements may be arranged as a plurality of strips and a plurality of depth segments, and the each edge-on detector module may further include a groove between at least two adjacent strips of the plurality of strips and a second anti-scatter structure. The second anti-scatter structure may be disposed inside the groove; the second anti-scatter structure may be configured to prevent or reduce scattering of photons between the at least two adjacent strips; and/or the anti-scatter structure may be configured to prevent or reduce scattering of photons between the each edge-on detector module and an adjacent detector module of the each edge-on detector module.

In some embodiments, the anti-scatter structure may be disposed on the second side of the each edge-on detector module; and/or the anti-scatter structure may be disposed on the backside electrode.

In some embodiments, the anti-scatter structure and the backside electrode may be made of a same material, and a thickness of the material may be greater than a second threshold; or the backside electrode may function as the anti-scatter structure, and a thickness of the backside electrode may be greater than the second threshold.

In some embodiments, the high atomic number material may include at least one of tungsten, plumbum, a tungsten alloy, or a plumbum alloy.

In some embodiments, the anti-scatter structure may be obtained by replacing one or more of the plurality of detection elements, and/or the backside electrode with one or more conductive high atomic number materials.

In some embodiments, the anti-scatter structure may be obtained by adding one or more high atomic number materials to the silicon substrate, one or more of the plurality of detection elements, and/or the backside electrode.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
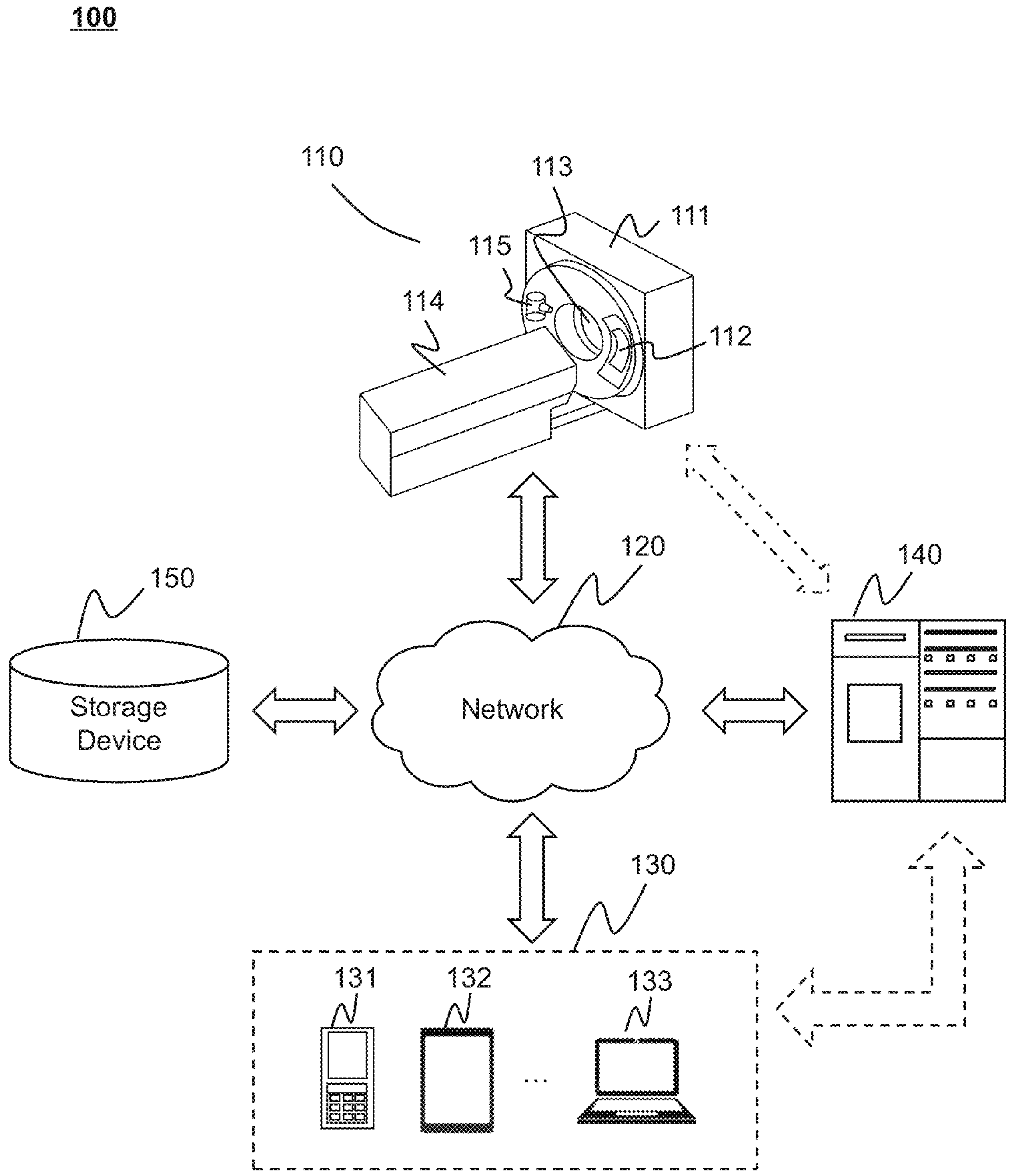
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for illustration and description only, and are not intended to limit the scope of the present disclosure. It is understood that the drawings are not to scale.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D) image, etc.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems for non-invasive biomedical imaging, such as for disease diagnostic or research purposes. In some embodiments, the systems may include a single modality imaging system and/or a multi-modality imaging system. The single modality imaging system may include, for example, a computed tomography (CT) system, or the like, or any combination thereof. The multi-modality imaging system may include, for example, a positron emission tomography-computed tomography (PET-CT) system. It should be noted that the imaging system described below is merely provided for illustration purposes, and not intended to limit the scope of the present disclosure.

The term "imaging modality" or "modality" as used herein broadly refers to an imaging method or technology that gathers, generates, processes, and/or analyzes imaging information of an object. The object may include a biological object and/or a non-biological object. The biological object may be a human being, an animal, a plant, or a portion thereof (e.g., a cell, a tissue, an organ, etc.). In some embodiments, the object may be a man-made composition of organic and/or inorganic matters that are with or without life.

An aspect of the present disclosure relates to a detector system. The detector system may include a plurality of edge-on detector modules. At least one of the edge-on detector modules may include a silicon substrate, a plurality of detection elements, a backside electrode, and an anti-scatter structure. The silicon substrate may include a front side corresponding to a first side of the edge-on detector module and a rear side corresponding to a second side of the edge-on detector module. The plurality of detection elements may be fabricated on the front side of the silicon substrate. The plurality of detection elements may be arranged as a plurality of strips and a plurality of depth segments. A backside electrode may be fabricated on the rear side of the silicon substrate. The anti-scatter structure may be fabricated on at least one of the first side or the second side of the edge-on detector module. The anti-scatter structure may be configured to prevent or reduce scattering of photons emitted into the silicon substrate. The silicon substrate, the plurality of detection elements, the backside electrode, and the anti-scatter structure may be configured as an integral piece.

According to some embodiments, the anti-scatter structure may be fabricated on the first side of the each edge-on detector module. The anti-scatter structure may include a plurality of anti-scatter units. Each anti-scatter unit of the plurality of anti-scatter units may correspond to one of the plurality of detection elements. In some embodiments, the anti-scatter structure may be fabricated on the second side of the each edge-on detector module. The anti-scatter structure may be fabricated on the backside electrode and/or electrically coupled to the backside electrode. That is to say, the anti-scatter structure may be integrated into the edge-on detector. Conventionally, the scattering of photons may be reduced by interfolding an anti-scatter module between at least a subset of edge-on detector modules. In contrast, the edge-on detector module of the present disclosure may prevent or reduce scattering of photons emitted into the silicon substrate without additional anti-scatter structures, which improves the performance of the plurality of edge-on detector modules. With the configuration of the edge-on detector modules of the present disclosure, scattering of photons between adjacent edge-on detector modules and scattering of photons between different detection elements in a same edge-on detector module may be reduced or prevented.

FIG. 1 is a schematic diagram illustrating an exemplary imaging system 100 according to some embodiments of the present disclosure. As shown, the imaging system 100 may include an imaging device 110, a network 120, one or more terminals 130, a processing device 140, and a storage device 150. In some embodiments, the imaging device 110, the terminal(s) 130, the processing device 140, and/or the storage device 150 may be connected to and/or communicate with each other via a wireless connection (e.g., the network 120), a wired connection, or a combination thereof. The connection between the components of the imaging system 100 may be variable. Merely by way of example, the imaging device 110 may be connected to the processing device 140 through the network 120, as illustrated in FIG. 1. As another example, the imaging device 110 may be connected to the processing device 140 directly. As a further example, the storage device 150 may be connected to the processing device 140 through the network 120, as illustrated in FIG. 1, or connected to the processing device 140 directly. As still a further example, a terminal 130 may be connected to the processing device 140 through the network 120, as illustrated in FIG. 1, or connected to the processing device 140 directly.

The imaging device 110 may generate or provide image data related to an object via scanning the object. In some embodiments, the object may include a biological object and/or a non-biological object. For example, the object may include a specific portion of a body, such as a head, a thorax, an abdomen, or the like, or a combination thereof. In some embodiments, the imaging device 110 may include a single-modality scanner (e.g., a CT scanner) and/or multi-modality scanner (e.g., a PET-CT scanner) as described elsewhere in this disclosure. In some embodiments, the image data relating to the object may include projection data, one or more images of the object, etc. The projection data may include raw data generated by the imaging device 110 by scanning the object and/or data generated by a forward projection on an image of the object.

In some embodiments, the imaging device 110 may include a gantry 111, a detector system 112, a detecting region 113, a scanning table 114, and a radioactive scanning source 115. The gantry 111 may support the detector system 112 and the radioactive scanning source 115. The object may be placed on the scanning table 114 to be scanned. The radioactive scanning source 115 may emit radioactive rays to the object. The radiation may include a particle ray, a photon ray, or the like, or a combination thereof. In some embodiments, the radiation may include a plurality of radiation particles (e.g., neutrons, protons, electron, μ-mesons, heavy ions), a plurality of radiation photons (e.g., X-ray, a γ-ray, ultraviolet, laser), or the like, or a combination thereof. The detector system 112 may detect radiations and/or radiation events (e.g., X-rays) from the detecting region 113. In some embodiments, the detector 112 may include a plurality of detector modules. The detector modules may include a scintillation detector (e.g., a cesium iodide detector) or a gas detector. The detector modules may be assembled as a single-row detector or a multi-rows detector. In some embodiments, the detector system may include a plurality of detector strips. In some embodiments, a strip detector that includes one or more detector strips may include a positive electrode surface and a negative electrode surface opposite to the positive electrode surface. By applying voltage to the positive electrode surface and the negative electrode surface, an electric field may be formed to detect X-rays passing through the object. A strip detector may include or be an edge-on detector module. In X-rays detection, an incidence direction of the X-rays may be substantially parallel to the two electrode surfaces of the edge-on detector module. In some embodiments, the edge-on detector module (also referred to as an edge-on strip detector) may include an edge-on silicon strip detector, for example, an edge-on silicon strip detector 200 shown in FIG. 2.

The network 120 may include any suitable network that can facilitate the exchange of information and/or data for the imaging system 100. In some embodiments, one or more components of the imaging system 100 (e.g., the imaging device 110, the processing device 140, the storage device 150, the terminal(s) 130) may communicate information and/or data with one or more other components of the imaging system 100 via the network 120. For example, the processing device 140 may obtain image data from the imaging device 110 via the network 120. As another example, the processing device 140 may obtain user instruction(s) from the terminal(s) 130 via the network 120.

The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may be connected to and/or communicate with the imaging device 110, the processing device 140, and/or the storage device 150. For example, the terminal(s) 130 may display an image of the object. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc. In some embodiments, the terminal(s) 130 may be part of the processing device 140.

The processing device 140 may process data and/or information obtained from the imaging device 110, the storage device 150, the terminal(s) 130, or other components of the imaging system 100. In some embodiments, the processing device 140 may be a single server or a server group. The server group may be centralized or distributed. In some embodiments, the processing device 140 may be local to or remote from the imaging system 100. For example, the processing device 140 may access information and/or data from the imaging device 110, the storage device 150, and/or the terminal(s) 130 via the network 120. As another example, the processing device 140 may be directly connected to the imaging device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof.

In some embodiments, the processing device 140 may include one or more processors (e.g., single-core processor(s) or multi-core processor(s)). Merely by way of example, the processing device 140 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 150 may store data, instructions, and/or any other information. In some embodiments, the storage device 150 may store data obtained from the processing device 140, the terminal(s) 130, and/or the imaging device 110. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the imaging system 100 (e.g., the processing device 140, the terminal(s) 130). One or more components of the imaging system 100 may access the data or instructions stored in the storage device 150 via the network 120. In some embodiments, the storage device 150 may be part of the processing device 140.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the imaging system 100 may include one or more additional components. Additionally or alternatively, one or more components of the imaging system 100 described above may be omitted. As another example, two or more components of the imaging system 100 may be integrated into a single component.

Figure 2:
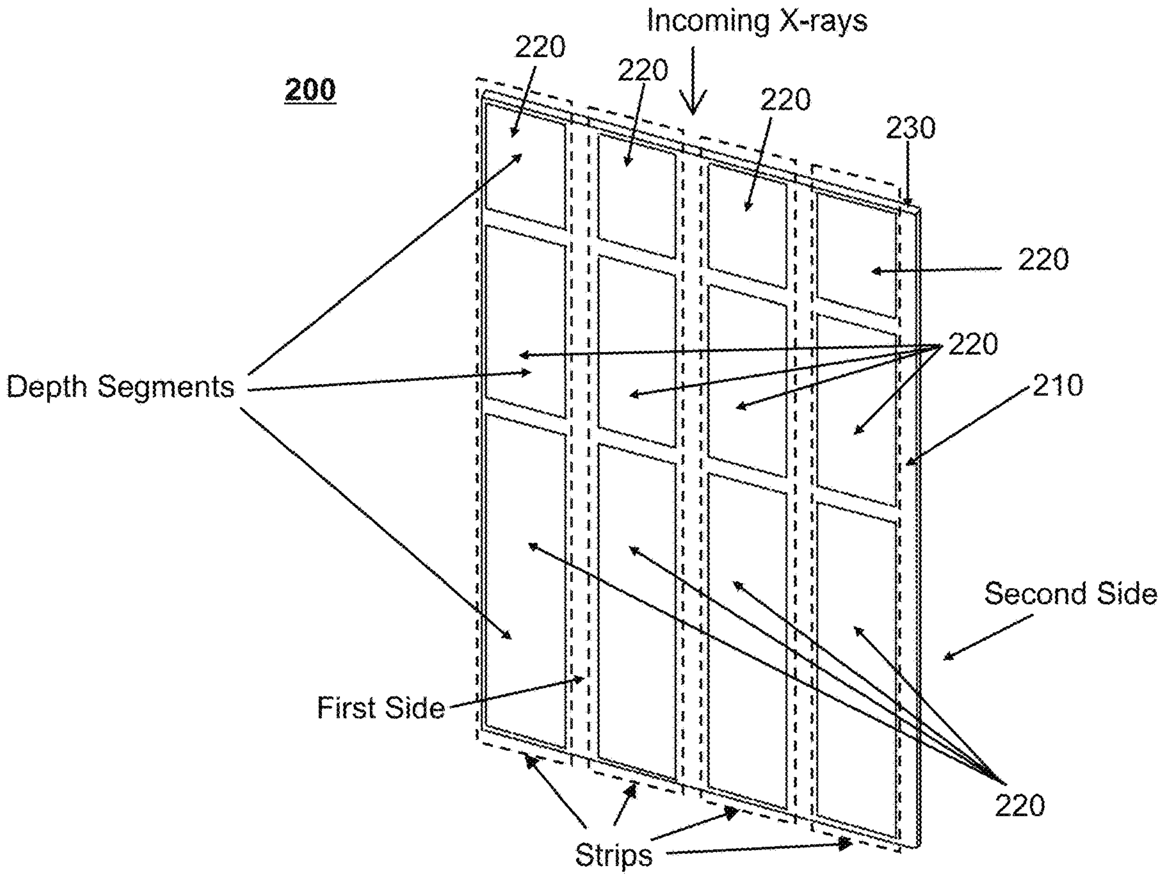
FIG. 2 is a schematic diagram illustrating an exemplary edge-on strip detector according to some embodiments of the present disclosure.

FIG. 2 is a schematic diagram illustrating an exemplary edge-on strip detector 200 according to some embodiments of the present disclosure. The edge-on strip detector 200 may be an exemplary edge-on detector module as described in FIG. 1. The edge-on strip detector 200 may be configured to detect X-rays through photon counting. As shown in FIG. 2, the edge-on strip detector 200 may have a first side and a second side opposite to each other. The edge-on strip detector 200 may include an incidence edge 230 adapted to be oriented towards an X-ray source (e.g., a radioactive scanning source 115) that generates X-rays. The edge-on strip detector 200 may include a substrate 210 (e.g., a silicon substrate) and a plurality of detection elements 220. In some embodiments, the substrate 210 may be a semiconductor substrate. The substrate 210 may include a front side corresponding to the first side of the edge-on strip detector 200 and a rear side corresponding to the second side of the edge-on strip detector 200. The front side and/or the rear side of the substrate 210 may be substantially parallel to an incidence direction of the X-rays. The plurality of detection elements 220 may be formed (or fabricated) or disposed on the front side of the substrate 210. The plurality of detection elements 220 may be arranged as a plurality of strips and a plurality of depth segments. Merely by way of example, as illustrated in FIG. 2 (which is merely provided for the purposes of illustration), the plurality of detection elements 220 may be arranged as four strips each of which may have three depth segments. In some embodiments, each of the plurality of strips may include one or more depth segments arranged along an incidence direction of the X-rays, thereby forming the plurality of detection elements 220. In some embodiments, each of the plurality of detection elements 220 may include or be an electrode (e.g., a conductive electrode). The plurality of detection elements 220 (or electrodes) may be formed (or fabricated) or disposed on the front side of the substrate 210. In some embodiments, the plurality of detection elements 220 (or electrodes) may be fabricated on the front side of the substrate 210 using microfabrication technology. Merely by way of example, a heavily doped layer may be formed or implanted on a plurality of regions on the front side of the substrate 210, and an electrode layer may be formed or implanted on the heavily doped layer in the plurality of regions to obtain the plurality of detection elements 220 (or electrodes). For instance, the plurality of detection elements 220 (or electrodes) may be fabricated on an n-type silicon substrate with p-type electrodes implanted.

In some embodiments, the edge-on strip detector 200 may further include a backside electrode (not shown) formed (or fabricated) or disposed on the rear side of the substrate 210. In some embodiments, the backside electrode may be fabricated on the rear side of the substrate 210 using microfabrication technology. Merely by way of example, a heavily doped layer may be formed or implanted on the rear side of the substrate 210, and an electrode layer may be formed or implanted on the heavily doped layer to obtain the backside electrode. For instance, the backside electrode may be fabricated on an n-type silicon substrate with n-type electrode implanted.

Thicknesses of the plurality of detection elements 220 (or electrodes) and/or the backside electrode may be within a range from 1 nm to 500 μm (or micrometers) (e.g., 1 nm-100 nm, 10 nm to 1 μm, 100 nm-1 μm, 100 nm-10 μm, 1 μm-10 μm, 1 μm-100 μm, 1 μm-500 μm, 10 μm-100 μm, 10 μm-500 μm, 100 μm-500 μm, etc.). In some embodiments, the plurality of detection elements 220 (or electrodes) may have a same thickness along a direction perpendicular to the substrate. In some embodiments, the plurality of detection elements 220 (or electrodes) may have different thicknesses. Merely by way of example, a thickness of a detection element (or electrode) may be related to a distance between the detection element (or electrode) and a source that emits photons (e.g., the X-ray source) (or the incidence edge 230). For instance, a thickness of a detection element (or electrode) that is relatively far away from the X-ray source (or the incidence edge 230) may be larger than that of a detection element (or electrode) that is relatively close to the X-ray source (or the incidence edge 230). In some embodiments, a depth (along the incidence direction of the X-rays) of the substrate 210 may be within a range from 1 cm-10 cm (e.g., 1 cm-5 cm, 2 cm-8 cm, 5 cm-10 cm, etc.). In some embodiments, a width of a detection element 220 may be within a range from 0.1 mm-2 mm. In some embodiments, an interval between two detection elements 220 may be within a range from 0.1 mm-2 mm. In some embodiments, a sum of the width of a detection element 220 and the interval between the detection element 220 and an adjacent detection element 220 may be within a range from 0.1 mm-2 mm.

In some embodiments, the plurality of depth segments in a strip (or each strip) may have different lengths along the incidence direction of the X-rays, such that approximately equal count rates are expected for the depth segments along the incidence direction of the X-rays and/or a count rate of each detection element is substantially averaged. For example, a length of a depth segment that is relatively far away from the X-ray source may be larger than that of a depth segment that is relatively close to the X-ray source. In some embodiments, depth segments at a same depth (e.g., depth segments having a same distance to the incidence edge 230) may have a same length along the incidence direction of the X-rays.

The plurality of detection elements 220 (or electrodes) and/or the backside electrode may be made of a conductive material. Exemplary conductive materials may include aluminum, copper, silver, tungsten, or the like. Merely by way of example, the detection elements and/or the backside electrode may include an aluminum electrode, a tungsten electrode, or the like. In some embodiments, two or more of the plurality of detection elements 220 (or electrodes) may be made of different materials. In some embodiments, at least one of the plurality of detection elements 220 (or electrodes) and the backside electrode may be made of different materials.

When the X-rays strike on the edge-on strip detector 200 and interact within the substrate of the edge-on strip detector 200 (that is, a photon interaction takes place in the substrate), electron-hole pairs may be produced. By applying an external bias voltage to a positive electrode surface (e.g., the backside electrode) and a negative electrode surface (e.g., each of the plurality of detection elements 220), the electron-hole pairs may be separated, and electrons may drift to the backside electrode, and holes may drift to the detection elements, thereby generating electrical signals (e.g., electrical pulses). The electrons drifting to the backside electrode and/or the holes drifting to the detection elements may also be referred to as drifting charges. The electrical pulses may be fed into an application specific integrated circuit (ASIC) channel for further processing, for example, being amplified, shaped, and/or converted to photon counts. The photon counts may be used to estimate an energy of the X-rays, and the energy of the X-rays may be used to reconstruct an image. The substrate may be made of a low atomic number material (e.g., silicon), which means the substrate may need to be made relatively thick (e.g., thicker than a threshold (e.g., several centimeters)) to achieve relatively high efficiency in absorbing the photons. However, it may be difficult to produce a face-on detector (the two electrode surfaces of which are perpendicular to the incidence direction of the X-rays) utilizing a substrate having a thickness of several centimeters. In contrast, the edge-on strip detector may have enough depth of the substrate along the incidence direction of the X-rays, which can facilitate the absorbing of most of photons without thickening the substrate. Thus, the edge-on strip detector 200 may be applied in an X-ray imaging system (e.g., the imaging device 110) to image an object.

Figure 3:
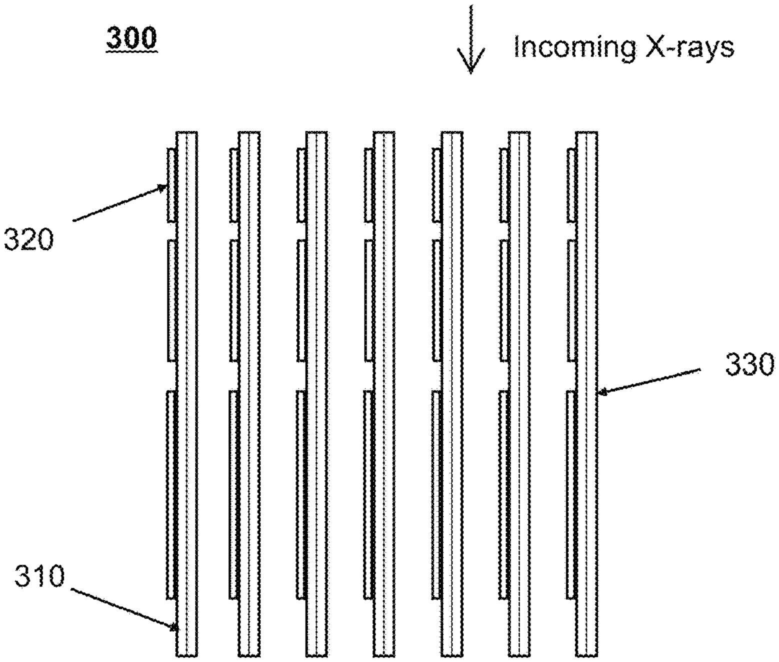
FIG. 3 is a schematic diagram illustrating an exemplary detector system according to some embodiments of the present disclosure.

FIG. 3 is a schematic diagram illustrating an exemplary detector system 300 according to some embodiments of the present disclosure. As shown in FIG. 3, the detector system 300 may include a plurality of edge-on detector modules. The edge-on detector modules may be positioned next to each other and configured to detect X-rays. Each edge-on detector module may include an incidence edge adapted to be oriented towards an X-ray source that generates X-rays. Each of the edge-on detector modules may have a structure that is similar to or the same as that of the edge-on strip detector 200. For example, each of the edge-on detector modules may include a substrate 310 (e.g., a silicon substrate) including a front side corresponding to a first side of the edge-on detector module and a rear side corresponding to a second side of the edge-on detector module, a plurality of detection elements 320 may be disposed (or fabricated) on the front side of the substrate 310, and a backside electrode 330 may be disposed (or fabricated) on the rear side of the substrate 310.

In general, photon interactions (e.g., a photoelectric effect) may take place in the low atomic number material (e.g., silicon), resulting scattering of photons. In some embodiments, the scattering of photons may include at least Compton scattering. The Compton scattering may occupy a relatively high fraction of the scattering of photons. For a detector system including a plurality of edge-on detector modules, scattered X-rays generated in an edge-on detector module due to Compton scattering may reach one or more other edge-on detector modules adjacent to the edge-on detector module, which may induce signal interferences among the plurality of edge-on detector modules. In addition, scattered X-rays generated (due to Compton scattering) in a detection element of an edge-on detector module may reach one or more other detection elements of the same edge-on detector module, which may induce signal interferences among the plurality of detection elements of the same edge-on detector module. The signal interferences among the edge-on detector modules and the signal interferences among the detection elements may degrade the performance of the detector system.

In some embodiments, the substrate 210 in FIG. 2 and/or the substrate 310 in FIG. 3 may be made of a material including a semiconductor (e.g., silicon, metal oxide, or gallium arsenide (GaAs), etc.).

In some embodiments, one or more (e.g., each) of the edge-on detector modules illustrated in FIGS. 2 and 3 may further include an anti-scatter structure. The anti-scatter structure may be configured to prevent or reduce scattering of photons emitted into the substrate 310. The scattering of photons may include scattering of photons between adjacent edge-on detector modules and/or scattering of photons between different detection elements in a same edge-on detector module. In some embodiments, the anti-scatter structure may be disposed (or fabricated) on the first side and/or the second side of the one or more (e.g., each) of the edge-on detector modules. In some embodiments, each of the edge-on detector modules may be equipped with one or more anti-scatter structures.

In some embodiments, the anti-scatter structure(s) may be integrated into each of the edge-on detector modules. In some embodiments, at least one of the edge-on detector modules may be configured as an integral piece. That is, the components (e.g., the substrate, the plurality of detection elements, the backside electrode, and/or the anti-scatter structure) of the at least one of the edge-on detector modules may be configured as an integral piece. In some embodiments, at least a portion of the anti-scatter structure may be implanted in or on the substrate (e.g., the front side and/or the rear side of the substrate), one or more of the detection elements, and/or the backside electrode. Merely by way of example, at least a portion of the anti-scatter structure may be fabricated, using microfabrication technology, on the substrate (see, e.g., FIGS. 5A, 5B, 8, 9A, and 9B), one or more of the detection elements (see, e.g., FIGS. 4B, 4C, 6A, 6B, and 6C), and/or the backside electrode (see, e.g., FIGS. 4A, 4C, and 7). Exemplary microfabrication techniques may include deposition or growth (e.g., thermal oxidation, chemical vapor deposition (CVD), physical vapor deposition (PVD) (e.g., sputtering, evaporative deposition, electron beam PVD)), epitaxy, patterning (e.g., photolithography, shadow masking), etching, or the like. In some embodiments, at least a portion of the anti-scatter structure may be coupled to (or implanted in/on, or fabricated on) the substrate (e.g., the front side and/or the rear side of the substrate), one or more of the detection elements, and/or the backside electrode via an insulating layer. In some embodiments, at least a portion of the anti-scatter structure may have a thickness within a range from 10 μm to 1000 μm (e.g., 10 μm-100 μm, 10 μm-200 μm, 10 μm-500 μm, 50 μm-100 μm, 50 μm-200 μm, 50 μm-500 μm, 100 μm-500 μm, 500 μm-1000 μm, etc.). In some embodiments, at least a portion of the anti-scatter structure may be coupled, through covalent bonds or metallic bonds, to the substrate (or an insulating layer thereon), one or more of the detection elements (or an insulating layer thereon), and/or the backside electrode (or an insulating layer thereon). In some embodiments, the insulating layer may be made of a material including silicon dioxide, silicon nitride, Teflon, plastic, polymer, etc. In some embodiments, the insulating layer may be disposed (or implanted, or fabricated) by, e.g., growth or deposition. The insulating layer may be configured to enhance connections between the anti-scatter structure and the substrate (or the one or more detection elements, or the backside electrode), and/or enhance anti-scatter functions of the anti-scatter structure. In some embodiments, at least a portion of the anti-scatter structure may be electrically coupled to one or more of the detection elements (see, e.g., FIGS. 4B-7) and/or the backside electrode (see, e.g., FIGS. 4A and 4C).

In some embodiments, the anti-scatter structure(s) may be obtained by fabricating the detection elements (or a portion thereof), the lead-out lines (or a portion thereof) of the detection elements, and/or the backside electrode (or a portion thereof) using one or more conductive high atomic number materials (e.g., tungsten), such that the detection elements (or a portion thereof), the lead-out lines (or a portion thereof) of the detection elements, and/or the backside electrode (or a portion thereof) can have both electrical conductivity and anti-scatter effect(s), and can function as the anti-scatter structure(s). In some embodiments, the conductive high atomic number materials may be conductive and may also provide an anti-scatter function. Alternatively, in some embodiments, the anti-scatter structure(s) may be obtained by replacing material(s) of the detection elements (or a portion thereof), the lead-out lines (or a portion thereof) of the detection elements, and/or the backside electrode (or a portion thereof) with one or more conductive high atomic number materials, such that the detection elements (or a portion thereof), the lead-out lines (or a portion thereof) of the detection elements, and/or the backside electrode (or a portion thereof) can have both electrical conductivity and anti-scatter effect(s), and can function as the anti-scatter structure(s) (e.g., the anti-scatter structure(s) shown in FIGS. 5A-6C and 8).

In some embodiments, the anti-scatter structure(s) may be obtained by adding (e.g., coupling, depositing, or growing) one or more high atomic number materials to or on the detection elements (or a portion thereof), the lead-out lines (or a portion thereof) of the detection elements, the backside electrode (or a portion thereof), and/or the substrate (or a portion thereof), such that the anti-scatter structure(s) can be fixedly attached to the detection elements (or a portion thereof), the lead-out lines (or a portion thereof) of the detection elements, the backside electrode (or a portion thereof), and/or the substrate (or a portion thereof) (e.g., the anti-scatter structure(s) shown in FIGS. 4A-4C, 7, and 9A-9B). In some embodiments, the anti-scatter structure(s) may be obtained by changing one or more dimensions of the detection elements (or a portion thereof), the lead-out lines (or a portion thereof) of the detection elements, and/or the backside electrode (or a portion thereof). For example, as shown in FIGS. 5A-6C, the anti-scatter structure(s) may be obtained by increasing the area(s) of the lead-out line(s) of the detection element(s). As another example, as shown in FIG. 8, the anti-scatter structure(s) may be obtained by increasing the thickness(es) of the detection element(s) and/or the backside electrode.

In some embodiments, the anti-scatter structure(s) may be made of a material including a conductive material (or at least a portion of the anti-scatter structure(s) may be conductive). In some embodiments, the anti-scatter structure(s) may be made of a material including a high atomic number material. In some embodiments, the high atomic number material may include tungsten, plumbum, a tungsten alloy, a plumbum alloy, titanium, chromium, manganese, iron, etc.

In some embodiments, the edge-on strip detector 200 may include a semiconductor substrate configured to transform photons into electrical signals, a plurality of detection elements and a backside electrode that are configured to collect the electrical signals, and/or an anti-scatter structure configured to reduce or prevent scattering of the photons at least between the edge-on strip detector 200 and one or more adjacent edge-on strip detectors. In some embodiments, the silicon substrate, the plurality of detection elements, the backside electrode, and the anti-scatter structure may be configured as an integral piece.

It should be noted that the contact between the semiconductor substrate and the detection element(s), between the semiconductor substrate and the backside electrode, between the semiconductor substrate and the anti-scatter structure, between the anti-scatter structure and the detection element(s), between the anti-scatter structure and the backside electrode, and/or between the anti-scatter structure and any other part of the detector system may be various. Merely by way of example, the anti-scatter structure may be disposed on, fabricated on, formed on, connected to (e.g., pasted to, attached to, fixed to) the semiconductor substrate, the detection element(s), the backside electrode, and/or any other part of the detector system (e.g., an insulating layer on the semiconductor substrate, the detection element(s), and/or the backside electrode).

The configuration of the anti-scatter structure(s) may be various. FIGS. 4A-9B provide exemplary edge-on detector modules equipped with exemplary anti-scatter structure(s). It should be noted that FIGS. 4A-9B and related descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, different edge-on detector modules may be equipped with different anti-scatter structure(s). Alternatively or additionally, one edge-on detector module may be equipped with two or more different anti-scatter structure(s). For example, one edge-on detector module may be equipped with a first anti-scatter structure configured to prevent or reduce scattering of photons between the one edge-on detector module and one or more adjacent edge-on detector modules, and a second anti-scatter structure configured to prevent or reduce scattering of photons among detection elements within the one edge-on detector module. In some embodiments, the silicon substrate illustrated in FIGS. 4A-9B may be replaced by a semiconductor substrate made of other materials, which are not limited herein.

Figure 4A:
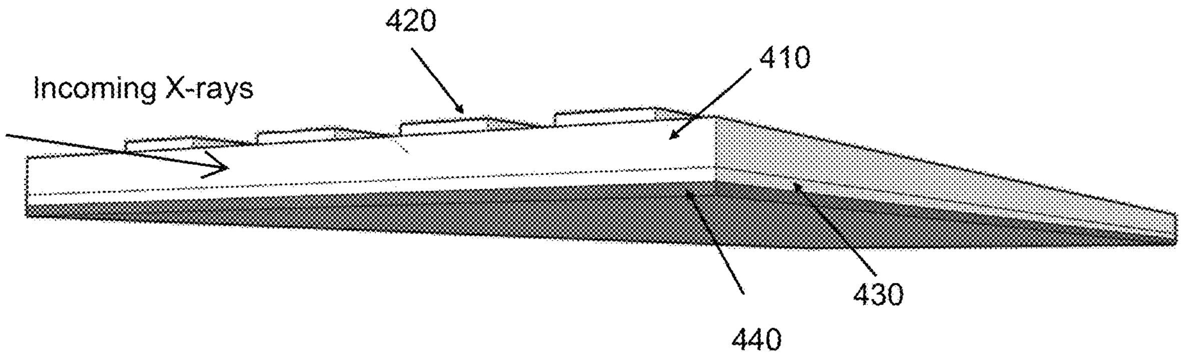
FIG. 4A is a schematic diagram illustrating an exemplary edge-on detector module according to some embodiments of the present disclosure.
Figure 4B:
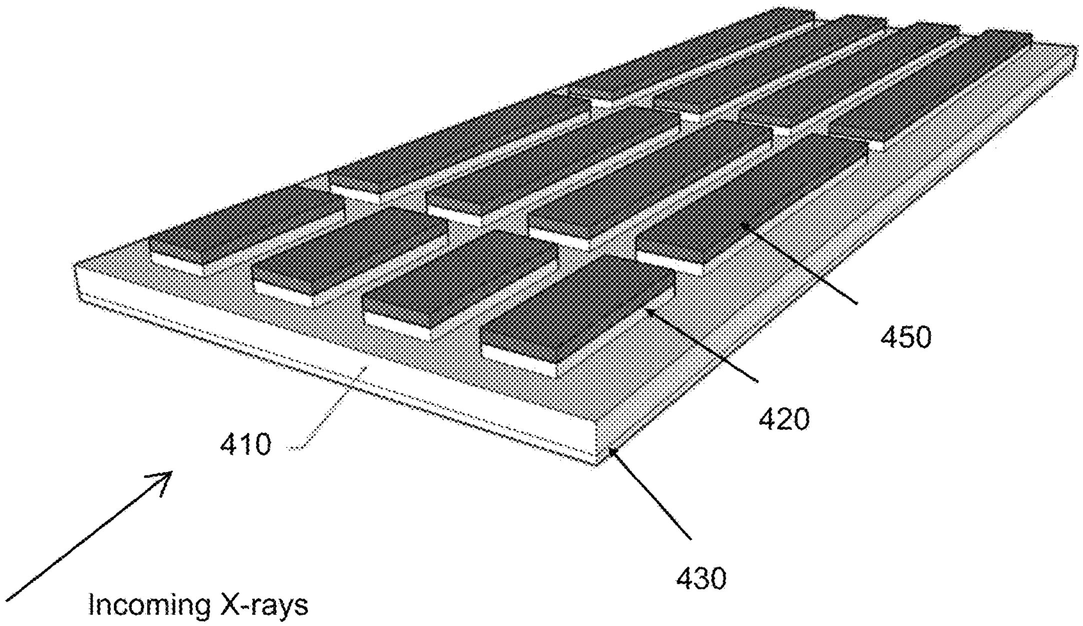
FIG. 4B is a schematic diagram illustrating an exemplary edge-on detector module according to some embodiments of the present disclosure.
Figure 4C:
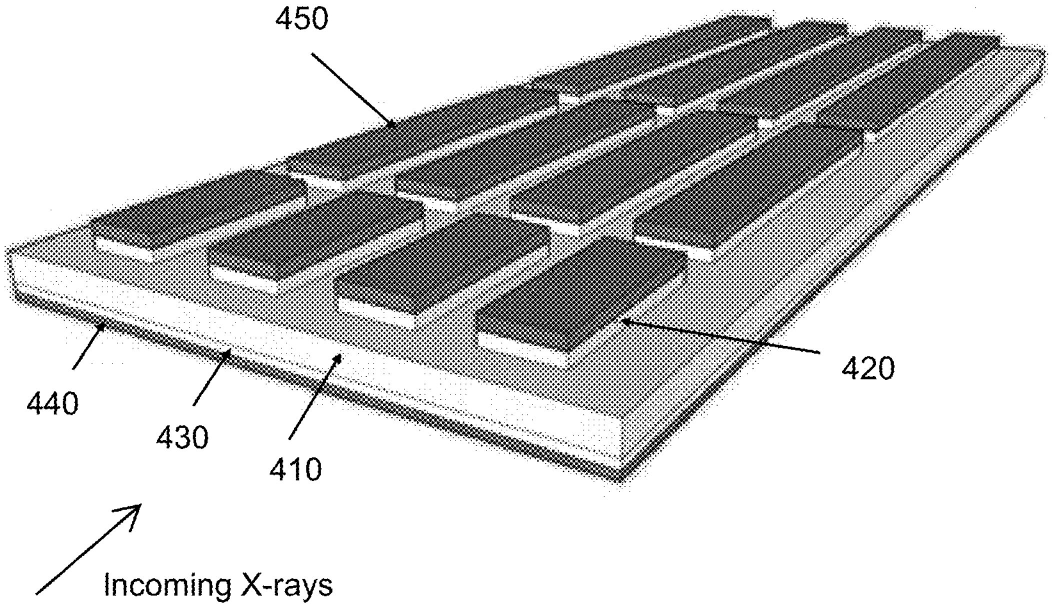
FIG. 4C is a schematic diagram illustrating an exemplary edge-on detector module according to some embodiments of the present disclosure.

In some embodiments, as shown in FIGS. 4B and 4C, an anti-scatter structure may be disposed (or fabricated) on the first side of an edge-on detector module. In some embodiments, the anti-scatter structure may include a plurality of anti-scatter units. In some embodiments, each anti-scatter unit of the plurality of anti-scatter units may correspond to one of the plurality of detection elements of the edge-on detector module. In some embodiments, at least one of the plurality of anti-scatter units may be disposed (or fabricated) on a corresponding detection element and/or electrically coupled to the corresponding detection element. In some embodiments, as shown in FIGS. 4A and 4C, an anti-scatter structure may be disposed (or fabricated) on the second side of an edge-on detector module. In some embodiments, the anti-scatter structure may be disposed (or fabricated) on the backside electrode and/or electrically coupled to the backside electrode.

FIG. 4A is a schematic diagram illustrating an exemplary edge-on detector module 400A according to some embodiments of the present disclosure. FIG. 4B is a schematic diagram illustrating an exemplary edge-on detector module 400B according to some embodiments of the present disclosure. FIG. 4C is a schematic diagram illustrating an exemplary edge-on detector module 400C according to some embodiments of the present disclosure.

As shown in FIG. 4A, the edge-on detector module 400A may include a silicon substrate 410, a plurality of detection elements 420, a backside electrode 430, and an anti-scatter structure 440. The edge-on detector module 400A may have a first side (e.g., an upper side of the edge-on detector module 400A) and a second side (e.g., a bottom side of the edge-on detector module 400A) opposite to each other. The silicon substrate 410 may include a front side corresponding to the first side of the edge-on detector module 400A and a rear side corresponding to the second side of the edge-on detector module 400A. The front side and the rear side of the silicon substrate 410 may be substantially parallel to an incidence direction of X-rays. The silicon substrate 410, the plurality of detection elements 420, and the backside electrode 430 may be similar to or the same as that of the edge-on strip detector 200. For example, the silicon substrate 410, the detection elements 420, and the backside electrode 430 may have a structure, a producing process, and/or a material that are the same as or similar to the silicon substrate 210, the detection elements 220, and the backside electrode of the edge-on strip detector 200, respectively. In some embodiments, the plurality of elements 420 and/or the backside electrode 430 may be aluminum electrodes. Aluminum is a low atomic number material, which may need to be relatively thick to be an efficient photon absorber. In some embodiments, photon interactions may take place in the silicon substrate and generate scattering of photons. In some embodiments, the backside electrode (e.g., aluminum electrode) may have a relatively small thickness, and the backside electrode may not block the scattering of photons between the edge-on detector module 400A and one or more adjacent edge-on detector modules. In some embodiments, in order to prevent or reduce scattering of photons emitted into and/or emitted out from the silicon substrate 410 through the backside electrode 430, the anti-scatter structure 440 may be disposed (or formed, or fabricated) on the second side of the edge-on detector module 400A. For example, the anti-scatter structure 440 may be disposed or formed on the backside electrode 430 and/or electrically coupled to the backside electrode 430. In some embodiments, the edge-on detector module 400A may further include one or more insulating layers between the backside electrode 430 and the anti-scatter structure 440. In some embodiments, the anti-scatter structure 440 may be fabricated on the second side of the edge-on detector module 400A (e.g., the backside electrode 430) using microfabrication technology. For example, the anti-scatter structure 440 may be disposed (or formed, or fabricated) on the backside electrode 430 through evaporation (e.g., chemical vapor deposition (CVD), physical vapor deposition (PVD)), sputtering, or any deposition or growth described in the present disclosure, or the like, or any combination thereof. In some embodiments, the anti-scatter structure 440 may have a shape and/or an area size that are the same as that of the backside electrode 430. In some embodiments, the anti-scatter structure 440 may be configured to reduce or prevent scattering of photons between the edge-on detector module 400A and one or more adjacent edge-on detector modules.

As shown in FIG. 4B, the edge-on detector module 400B may include a silicon substrate 410, a plurality of detection elements 420, a backside electrode 430, and an anti-scatter structure 450. The edge-on detector module 400B may have a first side (e.g., an upper side of the edge-on detector module 400B) and a second side (e.g., a bottom side of the edge-on detector module 400B) opposite to each other. The silicon substrate 410 may include a front side corresponding to the first side of the edge-on detector module 400B and a rear side corresponding to the second side of the edge-on detector module 400B. The front side and the rear side of the silicon substrate 410 may be substantially parallel to an incidence direction of X-rays. The edge-on detector module 400B may be similar to the edge-on detector module 400A, except that the anti-scatter structure 450 of the edge-on detector module 400B is disposed (or fabricated) on the first side of the edge-on detector module 400B rather than the second side of the edge-on detector module 400B. In some embodiments, the anti-scatter structure 450 may be configured as an integral structure, and the edge-on detector module 400B may further include one or more insulating layers between the plurality of detection elements 420 and the anti-scatter structure 450.

In some embodiments, as shown in FIG. 4B, the anti-scatter structure 450 may include a plurality of anti-scatter units. Each anti-scatter unit of the plurality of anti-scatter units may correspond to one of the detection elements 420. In some embodiments, at least one of the plurality of anti-scatter units may be disposed (or formed, or fabricated) on a corresponding detection element 420 and/or electrically coupled to the corresponding detection element 420. For example, the at least one of the plurality of anti-scatter units may be disposed (or fabricated) on the corresponding detection element through evaporation, sputtering, or the like. In some embodiments, the at least one of the plurality of anti-scatter units and the corresponding detection element of the plurality of detection elements may have a same shape and/or area size in a plane parallel to the front side of the silicon substrate. In some embodiments, the anti-scatter structure 450 may be configured to reduce or prevent scattering of photons between the edge-on detector module 400B and one or more adjacent edge-on detector modules and/or scattering of photons between different detection elements in the edge-on detector module 400B.

As shown in FIG. 4C, the edge-on detector module 400C may include a silicon substrate 410, a plurality of detection elements 420, a backside electrode 430, an anti-scatter structure 440, and an anti-scatter structure 450. The edge-on detector module 400C may be similar to the edge-on detector module 400A or the edge-on detector module 400B, except that both the first side and the second side of the edge-on detector module 400A or 400B are provided with an anti-scatter structure.

The anti-scatter structures 440 and/or 450 may be made of a material including a high atomic number material (e.g., tungsten, plumbum, a tungsten alloy, or a plumbum alloy, titanium, chromium, manganese, iron, etc.). By disposing (or forming, or fabricating) an anti-scatter structure on the detection elements 420 and/or the backside electrode 430, the scattering of photons may be reduced or prevented, which may prevent or reduce X-rays entering into and/or emitting out from the front side and/or the rear side of the silicon substrate 410 (that is induced by the scattering of photons and/or an alignment deviation of edge-on detector modules), thereby achieving an edge-on detector module with an anti-scatter function. In some embodiments, the anti-scatter structures 440 and/or 450 may be configured to reduce or prevent scattering of photons between the edge-on detector module 400C and one or more adjacent edge-on detector modules and/or scattering of photons between different detection elements in the edge-on detector module 400C. In addition, since the edge-on detector modules 400A-400C are fabricated based on a general edge-on detector module like the edge-on strip detector 200, a preparation technology of the edge-on detector modules 400A-400C may be mostly compatible with that of a general edge-on detector module, thereby reducing the difficulty in preparing the edge-on detector modules 400A-400C. In some embodiments, the anti-scatter structures 440 and 450 may be regarded as two separate anti-scatter structures. Alternatively, in some embodiments, the anti-scatter structures 440 and 450 may be regarded as two different portions of a single anti-scatter structure. In some embodiments, a thickness of the anti-scatter structures 440 and 450 may be 10 to 1000 μm, which may be larger than that of the detection element(s) 420.

Figure 5A:
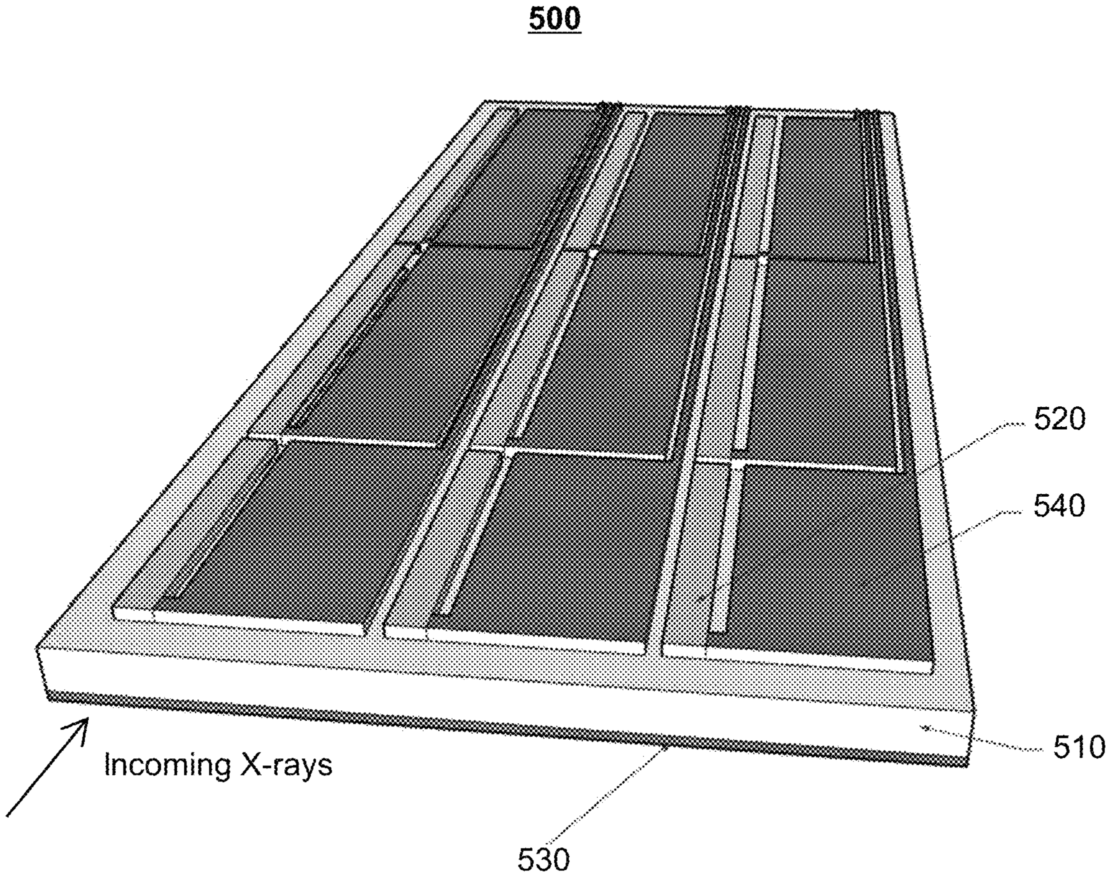
FIGS. 5A-5B are schematic diagrams illustrating an exemplary edge-on detector module according to some embodiments of the present disclosure.
Figure 5B:
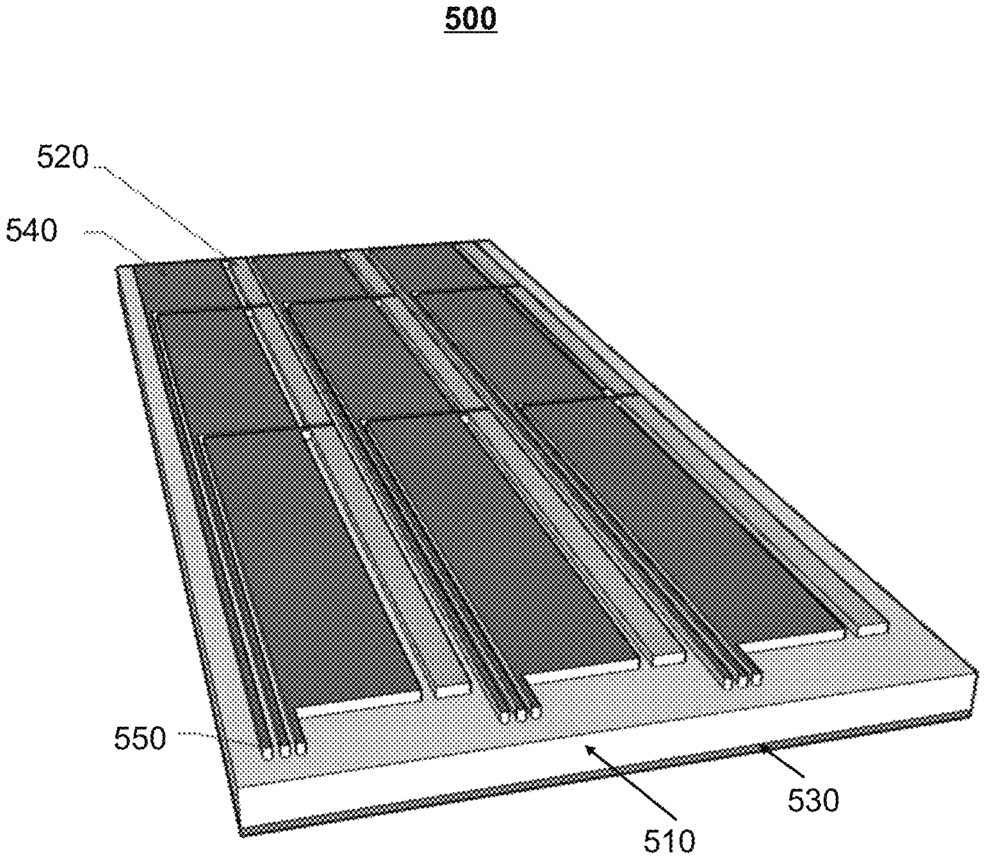

FIGS. 5A-5B are schematic diagrams illustrating an exemplary edge-on detector module 500 according to some embodiments of the present disclosure. As shown in FIGS. 5A and 5B, the edge-on detector module 500 may include a silicon substrate 510, a plurality of detection elements 520, a backside electrode 530, an anti-scatter structure 540, and a plurality of lead-out bonding pads 550. The edge-on detector module 500 may have a first side (e.g., an upper side of the edge-on detector module 500) and a second side (e.g., a bottom side of the edge-on detector module 500) opposite to each other. The silicon substrate 510 may include a front side corresponding to the first side of the edge-on detector module 500 and a rear side corresponding to the second side of the edge-on detector module 500. The front side and the rear side of the silicon substrate 510 may be substantially parallel to an incidence direction of X-rays. The detection elements 520 of the edge-on detector module 500 may be similar to that of the edge-on detector module 200 except that the detection elements 520 may have smaller area sizes and/or larger intervals than the detection elements 220 of the edge-on detector module 200.

As shown in FIGS. 5A and 5B, the anti-scatter structure 540 may include a plurality of anti-scatter units, and each anti-scatter unit of the plurality of anti-scatter units may correspond to one of the detection elements 520. At least one of the plurality of anti-scatter units may be disposed (or fabricated) on the front side of the silicon substrate 510, and accordingly, the at least one of the plurality of anti-scatter units may shield or cover a part of the front side of the silicon substrate 510. In some embodiments, the at least one of the plurality of anti-scatter units may be electrically coupled to a corresponding detection element 520. In some embodiments, at least one of the plurality of anti-scatter units may be coupled to the corresponding detection element 520 via an intermediate layer. In some embodiments, the intermediate layer may be made of a conducting material (e.g., a metal such as aluminum, a material of a lead-out line of the corresponding detection element 520). The intermediate layer may enhance the connection or coupling between the anti-scatter units and corresponding detection elements 520. An or each anti-scatter unit of the plurality of anti-scatter units may be configured as (or configured to perform as) a lead-out line of the corresponding detection element 520, and may be used to feed or transmit electrical signals (e.g., electrical pulses) detected by the detection element 520 into e.g., a corresponding ASIC channel for further processing. The plurality of anti-scatter units may be made of a material including a high atomic number material described elsewhere in the present disclosure (e.g., tungsten, plumbum, a tungsten alloy, or a plumbum alloy, etc.). In some embodiments, an area size of at least one of the plurality of anti-scatter units may be larger than that of a corresponding detection element 520. In some embodiments, a size (e.g., a length, a width, or an area size, etc.) of at least one of the plurality of anti-scatter units on the front side may be greater than a first threshold (e.g., a size (e.g., a length, a width, or an area size, etc.) of a lead-out line of an existing (e.g., a common or traditional) edge-on detector module). In some embodiments, the first threshold may be determined by the imaging system 100, or may be preset by a user or operator via the terminal(s) 130. In comparison with the existing edge-on detector module, due to the high atomic number material and the area size greater than the first threshold, the plurality of anti-scatter units may shield a relatively large region of the front side of the silicon substrate 510, and may have a relatively high photon absorption efficiency, thereby preventing or reducing scattering of photons emitted into the silicon substrate 510. In some embodiments, the anti-scatter structure 540 may be configured to reduce or prevent scattering of photons between the edge-on detector module 500 and one or more adjacent edge-on detector modules and/or scattering of photons between different detection elements 520 in the edge-on detector module 500. In some embodiments, due to the size (e.g., a length, a width, or an area size, etc.) of the anti-scatter unit(s) greater than the first threshold, a size (e.g., a length, a width, or an area size, etc.) of the plurality of detection elements may be reduced. In some embodiments, the plurality of detection elements may also be referred to as pixel electrodes (or pixels). With reduced sizes, the plurality of detection elements may have a relatively fast response time to drifting charges. That is, most of the electrical signals may be induced on the detection elements only shortly before the drifting charges could arrive at the detection elements, which may be also referred to as a small pixel effect. With reduced sizes, the detection elements may make use of the small pixel effect, thereby reducing a signal loss and improving a signal readout speed.

In some embodiments, the plurality of anti-scatter units may be not connected to each other. In some embodiments, two or more of the plurality of anti-scatter units may be insulated from each other via, e.g., an insulating layer, which may prevent a leakage current flowing between the two or more anti-scatter units from affecting signals detected by the corresponding detection elements 520. In some embodiments, the plurality of anti-scatter units may be insulated from each other.

In some embodiments, at least one of the plurality of anti-scatter units may be disposed (or implanted, or fabricated) on or coupled to the front side of the silicon substrate 510 through an insulating layer. In some embodiments, the insulating layer may be configured to enhance the connections between the at least one anti-scatter unit and the silicon substrate 510. In some embodiments, the insulating layer may be configured to enhance the anti-scatter function of the at least one anti-scatter unit. Merely by way of example, the edge-on detector module 500 may include an insulating layer between each of the at least one of the plurality of anti-scatter units and the front side of the silicon substrate.

In some embodiments, the lead-out bonding pads 550 may be disposed (or implanted, or fabricated) on the front side of the silicon substrate 510 and may be configured to facilitate connections between the anti-scatter structure 540 (that function as the lead-out lines of the corresponding detection elements 520) to a package chip (e.g., an ASIC channel).

It should be noted that the above description of the edge-on detector module 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, an anti-scatter unit of the anti-structure 540 may be in any other suitable shape, for example, an oval, a polygon. In some embodiments, a relative position between an anti-scatter unit of the anti-structure 540 and the corresponding detection element 520 may be various. For example, the anti-scatter unit may be parallel to the corresponding detection element 520. As another example, the anti-scatter unit may enclose the corresponding detection element 520 on a plane parallel to the incidence direction of the X-rays.

Figure 6A:
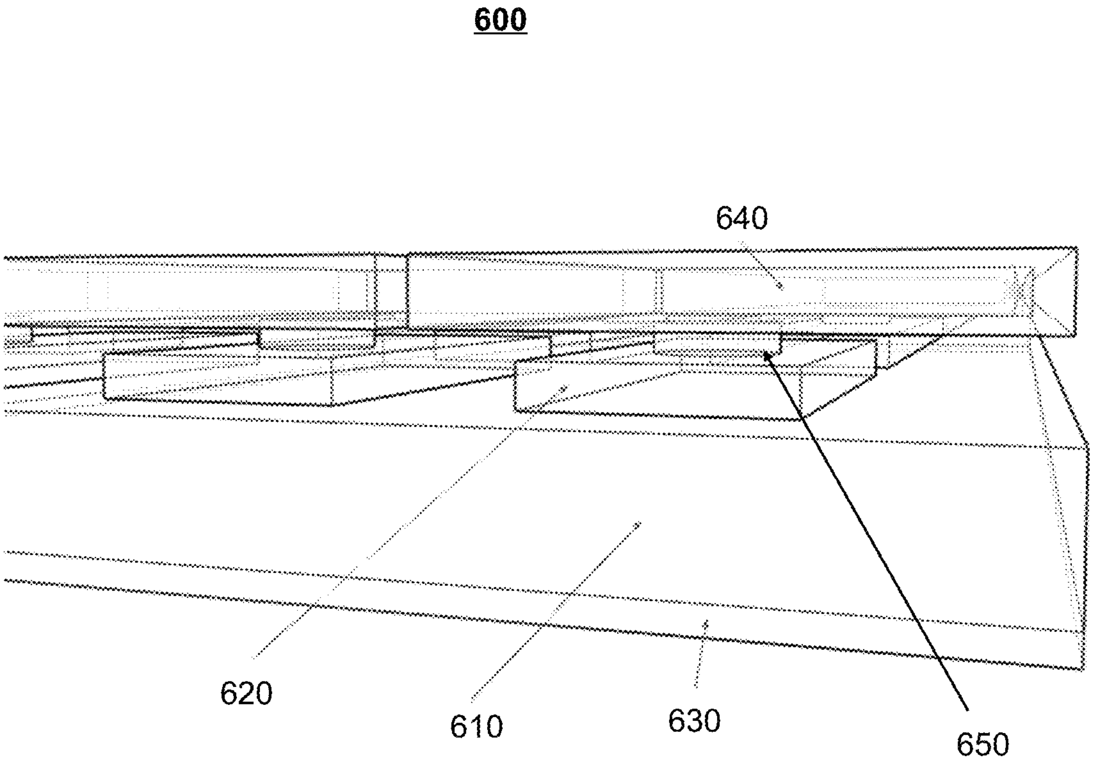
FIGS. 6A-6C are schematic diagrams illustrating an exemplary edge-on detector module according to some embodiments of the present disclosure.
Figure 6B:
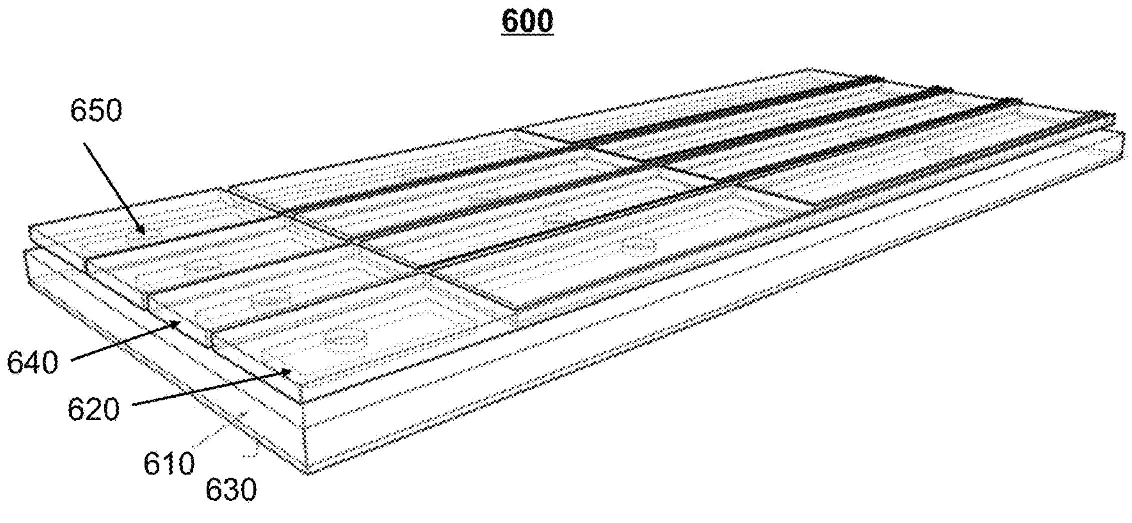
Figure 6C:
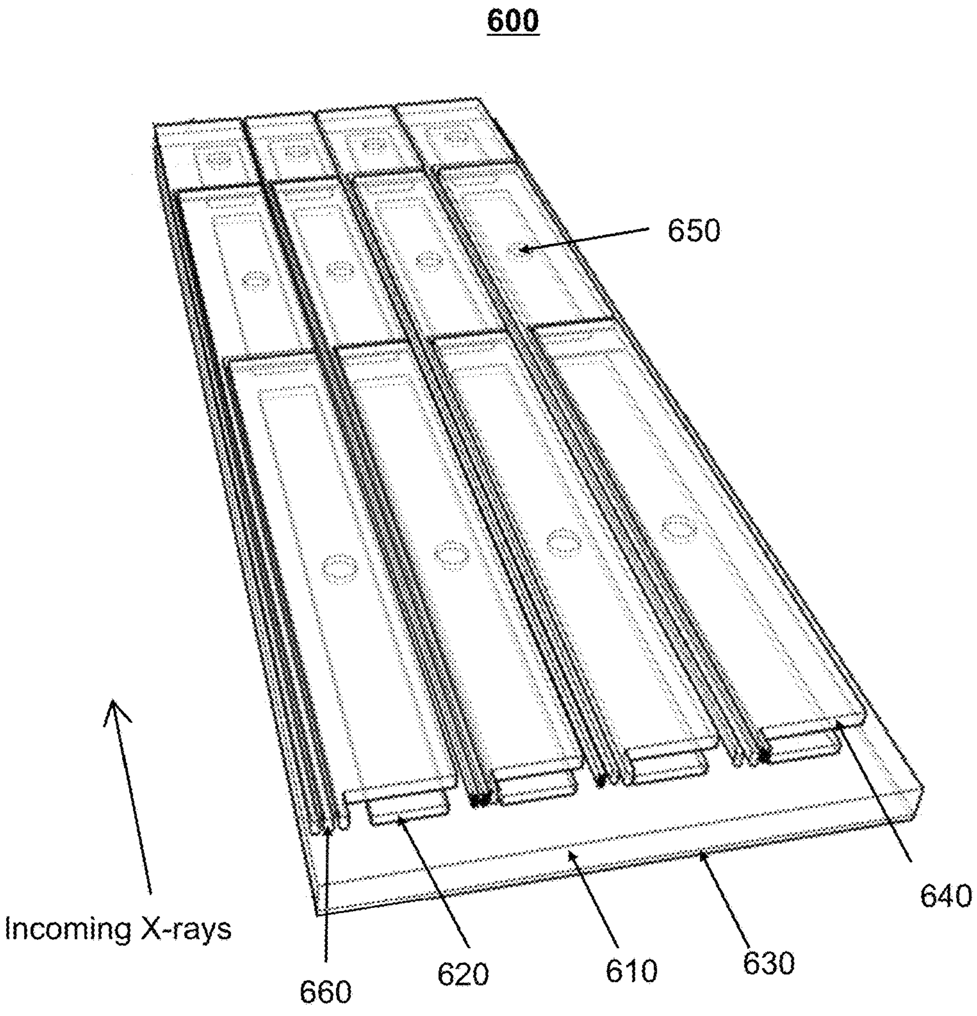

FIGS. 6A-6C are schematic diagrams illustrating an exemplary edge-on detector module 600 according to some embodiments of the present disclosure. As shown in FIGS. 6A-6C, the edge-on detector module 600 may include a silicon substrate 610, a plurality of detection elements 620, a backside electrode 630, an anti-scatter structure 640, and one or more connecting parts 650. The edge-on detector module 600 may have a first side (e.g., an upper side of the edge-on detector module 600) and a second side (e.g., a bottom side of the edge-on detector module 600) opposite to each other. The silicon substrate 610 may include a front side corresponding to the first side of the edge-on detector module 600 and a rear side corresponding to the second side of the edge-on detector module 600. The front side and the rear side of the silicon substrate 610 may be substantially parallel to an incidence direction of X-rays. The edge-on detector module 600 may be similar to the edge-on detector module 400B except the anti-scatter structure 640 and the connecting parts 650. In some embodiments, the anti-scatter structure 640 may be configured to reduce or prevent scattering of photons between the edge-on detector module 600 and one or more adjacent edge-on detector modules and/or scattering of photons between different detection elements 620 in the edge-on detector module 600.

As shown in FIGS. 6A-6C, the anti-scatter structure 640 may include a plurality of anti-scatter units, and each anti-scatter unit of the plurality of anti-scatter units may correspond to one of the detection elements 620. At least one of the plurality of anti-scatter units may be disposed (or fabricated) on a corresponding detection element. In some embodiments, the at least one of the plurality of anti-scatter units may be electrically coupled to the corresponding detection element 620 via a corresponding connecting part 650. In some embodiments, the connecting part 650 may be made of a conducting material (e.g., a conducting metal such as silver, copper, gold, or the like). The connecting part 650 may be configured to connect (e.g., conductively connect) the anti-scatter unit and the corresponding detection element 620.

In some embodiments, the connecting part 650 may be disposed (or implanted, or fabricated) on and/or electrically coupled to the detection element 620, and the anti-scatter unit may be disposed (or implanted, or fabricated) on and/or electrically coupled to the connecting part 650. Alternatively, in some embodiments, the connecting part 650 may be inserted into the detection element 620 and/or the anti-scatter unit.

Merely by way of example, in some embodiments, at least one of the plurality of anti-scatter units may be electrically coupled to the corresponding detection element 620 via a conducting material (described elsewhere in the present disclosure) filled in a hole (e.g., a through hole) of the at least one of the plurality of anti-scatter units. In some embodiments, the through hole may run through the at least one of the plurality of anti-scatter units and the corresponding detection element 620. For instance, the at least one anti-scatter unit may be disposed (or implanted, or fabricated) on the corresponding detection element 620. In some embodiments, an insulating layer may be disposed (or implanted, or fabricated) between the at least one anti-scatter unit and the corresponding detection element 620 to enhance the connection between and/or insulate the at least one anti-scatter unit and the corresponding detection element 620. Subsequently, the hole (e.g., through hole) may be generated or formed through etching, and then the conducting material may be disposed (or filled, or fabricated) in the hole to obtain the connecting part 650.

In some embodiments, an anti-scatter unit of the anti-scatter structure 640 may be configured as a lead-out line of the corresponding detection element 620. The plurality of anti-scatter units may be made of a material including a high atomic number material described elsewhere in the present disclosure (e.g., tungsten, plumbum, a tungsten alloy, or a plumbum alloy, etc.). In some embodiments, at least one of the plurality of anti-scatter units may completely shield a corresponding detection element 620. To this end, a size (in a plane parallel to the front side of the silicon substrate) of the at least one anti-scatter unit may be greater than a size of the corresponding detection element 620. In some embodiments, the at least one anti-scatter unit may enclose the corresponding detection element 620. In some embodiments, the corresponding detection element 620 may be embedded in the at least one anti-scatter unit.

In some embodiments, the plurality of anti-scatter units may be not connected to each other. In some embodiments, the at least one anti-scatter unit may include two anti-scatter units insulated from each other (i.e., two or more of the plurality of anti-scatter units may be insulated from each other) via, e.g., an insulating layer, which may prevent a leakage current flowing between the two or more anti-scatter units from affecting signals detected by the corresponding detection elements 620. In some embodiments, the plurality of anti-scatter units may be insulated from each other.

In some embodiments, similar to the edge-on detector module 500, the edge-on detector module 600 may further include a plurality of lead-out bonding pads (not shown). In some embodiments, an anti-scatter unit of the anti-structure 640 may be in any other suitable shape. For example, the anti-scatter unit may be in a shape of an oval, a polygon, or the like. As another example, the anti-scatter unit may include a curved surface. Merely by way of example, a portion of the anti-scatter unit covering the corresponding detection element 620 may be flat and have the same size and shape as the corresponding detection element 620, and the remaining portion of the anti-scatter unit may be curved and extend to the silicon substrate 610 (or the insulating layer disposed between the anti-scatter unit and the corresponding detection element 620). In some embodiments, a relative position between an anti-scatter unit of the anti-structure 640 and the corresponding detection element 620 may be various. For example, the anti-scatter unit may be parallel to the corresponding detection element 620. As another example, the anti-scatter unit may enclose the corresponding detection element 620.

Figure 7:
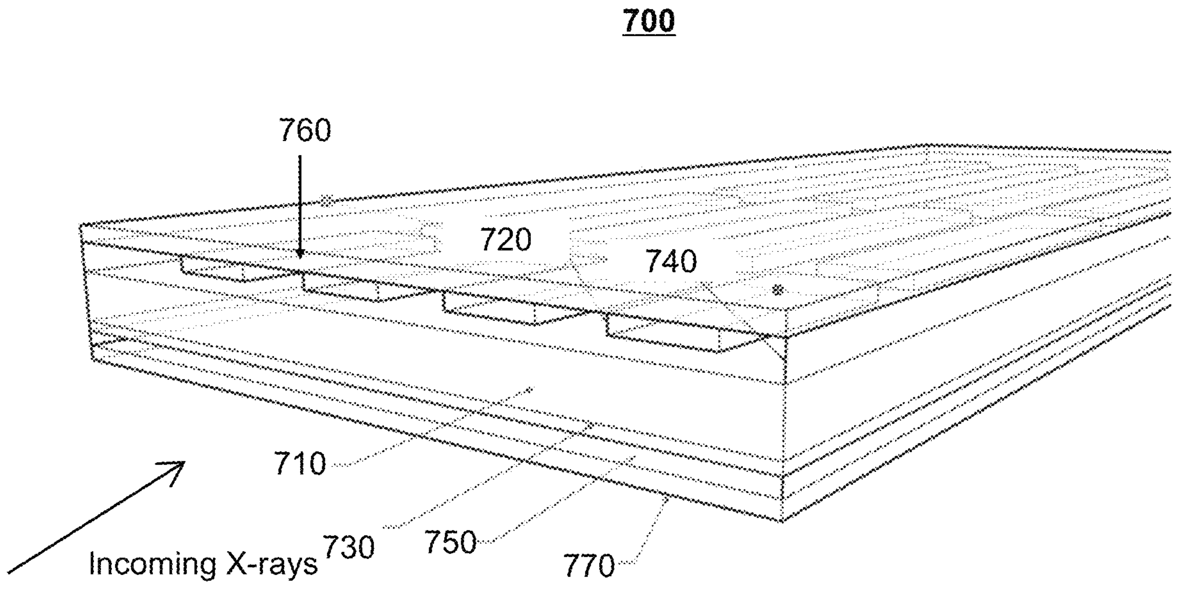
FIG. 7 is a schematic diagram illustrating an exemplary edge-on detector module according to some embodiments of the present disclosure.
Figure 8:
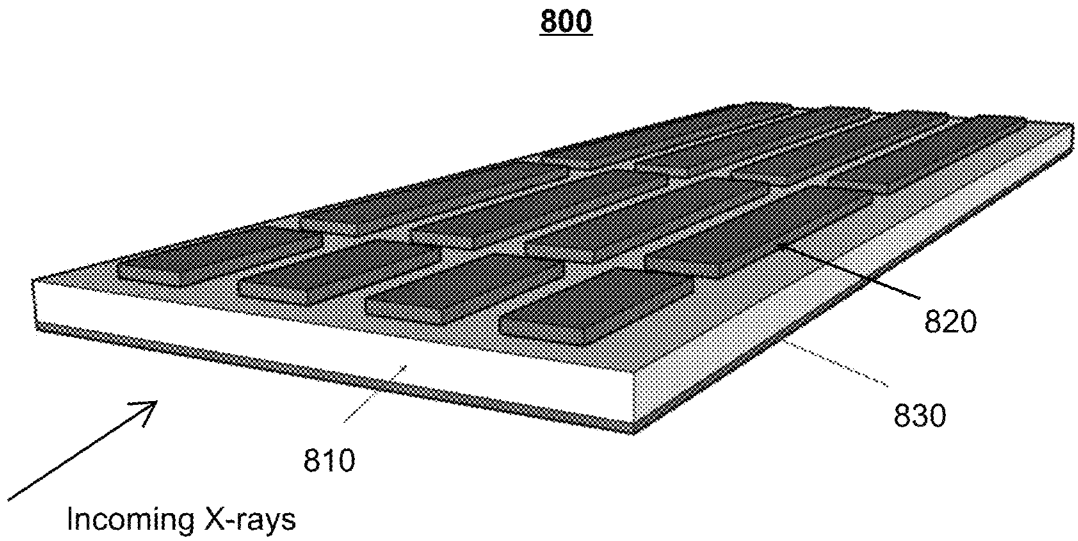
FIG. 8 is a schematic diagram illustrating an exemplary edge-on detector module according to some embodiments of the present disclosure.

FIG. 7 is a schematic diagram illustrating an exemplary edge-on detector module 700 according to some embodiments of the present disclosure. As shown in FIG. 7, the edge-on detector module 700 may include a silicon substrate 710, a plurality of detection elements 720, a backside electrode 730, a first insulating layer 740, a second insulating layer 750, a first anti-scatter structure 760, and/or a second anti-scatter structure 770. The edge-on detector module 700 may have a first side (e.g., an upper side of the edge-on detector module 700) and a second side (e.g., a bottom side of the edge-on detector module 700) opposite to each other. The silicon substrate 710 may include a front side corresponding to the first side of the edge-on detector module 700 and a rear side corresponding to the second side of the edge-on detector module 700. The front side and the rear side of the silicon substrate 710 may be substantially parallel to an incidence direction of X-rays. The edge-on detector module 700 may be similar to the edge-on detector module 400C, except that the edge-on detector module 700 includes the first insulating layer 740 and the second insulating layer 750.

The first insulating layers 740 may insulate the detection elements 720 from the first anti-scatter structure 760, and/or the second insulating layer 750 may insulate the backside electrode 730 from the second anti-scatter structure 770, thereby preventing the anti-scatter structures 760 and/or 770 from affecting signals detected by the plurality of detection elements 720, respectively. In some embodiments, the first insulating layer 740 may be disposed between the first anti-scatter structure 760 and the silicon substrate 710. In some embodiments, the second insulating layer 750 may be disposed between the second anti-scatter structure 770 and the silicon substrate 710. As used herein, the first insulating layer 740 being disposed between the first anti-scatter structure 760 and the silicon substrate 710 refers that the first insulating layer 740 may be disposed (or fabricated) on the front side of the silicon substrate 710 and/or the detection element(s) 720, as long as the first insulating layer 740 may insulate the detection element(s) 720 and the first anti-scatter structure 760. For example, the first insulating layer 740 may be disposed (or fabricated) on the front side of the silicon substrate 710. As used herein, the second insulating layer 750 being disposed between the second anti-scatter structure 770 and the silicon substrate 710 refers that the second insulating layer 750 may be disposed between the backside electrode 730 and the second anti-scatter structure 770, so as to insulate the backside electrode 730 and the second anti-scatter structure 770. For example, the second insulating layer 750 may be disposed (or fabricated) on the backside electrode 730, and have the same shape and area size as the backside electrode 730. In some embodiments, through the insulating layers 740 and 750, a relatively large-area anti-scatter structure (e.g., a continuous anti-scatter layer) may be achieved, and the anti-scatter structure may further have an electromagnetic shielding function. In some embodiments, the insulating layers 740 and/or 750 may be fabricated using an insulating material with high atomic number, so that the insulating layers 740 and/or 750 may prevent or reduce scattering of photons emitted into the silicon substrate 710. In some embodiments, the anti-scatter structures 760 and/or 770 may be configured to reduce or prevent scattering of photons between the edge-on detector module 700 and one or more adjacent edge-on detector modules and/or scattering of photons between different detection elements 720 in the edge-on detector module 700. In some embodiments, the anti-scatter structures 760 and/or 770 may have relatively large thicknesses (e.g., 10 μm-500 μm). It should be noted that the insulating layers 740 and 750 are merely provided for illustration, and some alternatives, modifications, and variations will be apparent to those skilled in the art. For example, the edge-on detector module 700 may only include the first insulating layer 740 or the second insulating layer 750. As another example, the first insulating layer 740 may be disposed (or fabricated) on both the front side of the silicon substrate 710 and the detection element(s) 720.

Alternatively or additionally, in some embodiments, the anti-scatter structures 760 and 770 may be similar to the anti-scatter structure 440 of the edge-on detector module 400A. In some embodiments, although not shown, the first anti-scatter structure 760 may be similar to the anti-scatter structure 450 including a plurality of anti-scatter units. In some embodiments, a preparation technology of the edge-on detector module 700 may be compatible with that of a general edge-on detector module, thereby reducing the difficulty in preparing the edge-on detector module 700.

In some embodiments, thicknesses of the anti-scatter structures of the edge-on detector modules 400A-700 may be set according to actual requirements. In some embodiments, the plurality of anti-scatter units of an anti-scatter structure may have a same thickness along a direction perpendicular to the silicon substrate. In some embodiments, the plurality of anti-scatter units of an anti-scatter structure may have different thicknesses along the direction perpendicular to the silicon substrate, and a thickness of an anti-scatter unit of the plurality of anti-scatter units may be related to a distance between the anti-scatter unit and a source that emits the photons. For example, if the anti-scatter unit is relatively close to an X-ray source, a relatively large amount of photons may be emitted into the silicon substrate, and thus, the anti-scatter unit may need to have a relatively large thickness. In some embodiments, a thickness of one (or each) of the anti-scatter units may be within a suitable range, so as to achieve a good anti-scatter effect and avoid the incoming X-rays from striking on the anti-scatter units and affecting a detection efficiency of the edge-on detector module. In some embodiments, the thickness(es) of the anti-scatter unit(s) may be within a range from 1 μm to 1000 μm (e.g., 10 μm-1000 μm, 10 μm-100 μm, 100 μm-500 μm, 500 μm-1000 μm, etc.). Merely by way of example, if at least one of the anti-scatter units includes tungsten, the thickness (along a direction perpendicular to the silicon substrate) of the at least one anti-scatter unit may be within a range from 10 μm to 1000 μm, e.g., 50 μm, 100 μm, 200 μm, etc. In some embodiments, different anti-scatter structures disposed (or fabricated) on different sites of an edge-on detector module may have different thicknesses. Merely by way of example, anti-scatter structures respectively coupled to the detection elements and backside electrode may have different thicknesses. For instance, the anti-scatter structures 760 and 770 in FIG. 7 (and/or the anti-scatter structures 440 and 450 in FIG. 4C) may have different thickness.

It should be noted that the above descriptions regarding FIGS. 2-7 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the plurality of anti-scatter units of the edge-on detector modules 500 and 600 may be in any suitable shape, for example, a rectangle, a circle. In some embodiments, the anti-scatter structures 760 and 770 may be regarded as two separate anti-scatter structures. Alternatively, in some embodiments, the anti-scatter structures 760 and 770 may be regarded as two different portions of a single anti-scatter structure.

FIG. 8 is a schematic diagram illustrating an exemplary edge-on detector module 800 according to some embodiments of the present disclosure. As shown in FIG. 8, the edge-on detector module 800 may include a silicon substrate 810, a plurality of detection elements 820, and a backside electrode 830. In some embodiments, the detection elements 820 and/or the backside electrode 830 may be made of a material including a high atomic number material. In some embodiments, through thickening the detection elements 820 and/or the backside electrode 830, the detection elements 820 and/or the backside electrode 830 may prevent or reduce scattering of photons emitted into the silicon substrate 810. That is, the detection elements 820 and/or the backside electrode 830 may also function as the anti-scatter structure(s). Accordingly, a detection element 820 may function as an anti-scatter unit. In some embodiments, both the detection elements 820 and the backside electrode 830 may function as anti-scatter structures. In some embodiments, the thicknesses of the detection elements 820 and/or the backside electrode 830 may be larger than a second threshold. The second threshold may be determined by the imaging system 100, or may be preset by a user or operator via the terminal(s) 130. In some embodiments, the second threshold (e.g., tungsten electrode) may be no less than 10 μm. For example, the thickness of each of the plurality of detection elements 820 may be no less than 40 μm. As another example, the thickness of the backside electrode 830 may be no less than 40 μm. In some embodiments, the anti-scatter structure (e.g., the detection elements 820, and/or the backside electrode 830) may also be configured to reduce or prevent scattering of photons between the edge-on detector module 800 and one or more adjacent edge-on detector modules and/or scattering of photons between different detection elements 820 in the edge-on detector module 800.

In some embodiments, the edge-on detector module 800 may further include an anti-scatter structure disposed (or fabricated) on the detection elements 820, the anti-scatter structure and the plurality of detection elements 820 may be made of a same material, and a thickness of the material may be no less than the second threshold. In other words, the plurality of detection elements 820 may function as the anti-scatter structure (i.e., a detection element 820 may function as an anti-scatter unit), and a thickness of each of the plurality of detection elements 820 may be no less than the second threshold. In some embodiments, the material may include any high atomic number material (e.g., a high atomic number material described in the present disclosure such as tungsten).

In some embodiments, the edge-on detector module 800 may further include an anti-scatter structure disposed (or fabricated) on the backside electrode 830, the anti-scatter structure and the backside electrode 830 may be made of a same material, and a thickness of the material may be no less than the second threshold. In other words, the backside electrode 830 may functions as the anti-scatter structure, and a thickness of the backside electrode 830 may be no less than the second threshold.

In some embodiments, for an edge-on detector module, the plurality of anti-scatter units corresponding the plurality of detection elements may be the same (or similar) or different. For example, one or more of the plurality of anti-scatter units may be the same as or similar to the anti-scatter units of the anti-scatter structure 450 illustrated in FIGS. 4B and 4C, while one or more other anti-scatter units may be the same as or similar to the anti-scatter units of the anti-scatter structure 540. As another example, one or more of the plurality of anti-scatter units may be the same as or similar to the anti-scatter units of the anti-scatter structure 640, while one or more other anti-scatter units may be the same as or similar to the detection elements 820. As still another example, one or more of the plurality of anti-scatter units may be the same as or similar to the anti-scatter units of the anti-scatter structure 450, while one or more other anti-scatter units may be the same as or similar to the anti-scatter units of the first anti-scatter structure 760 that is insulated from the silicon substrate via the first insulating layer 740.

Figure 9A:
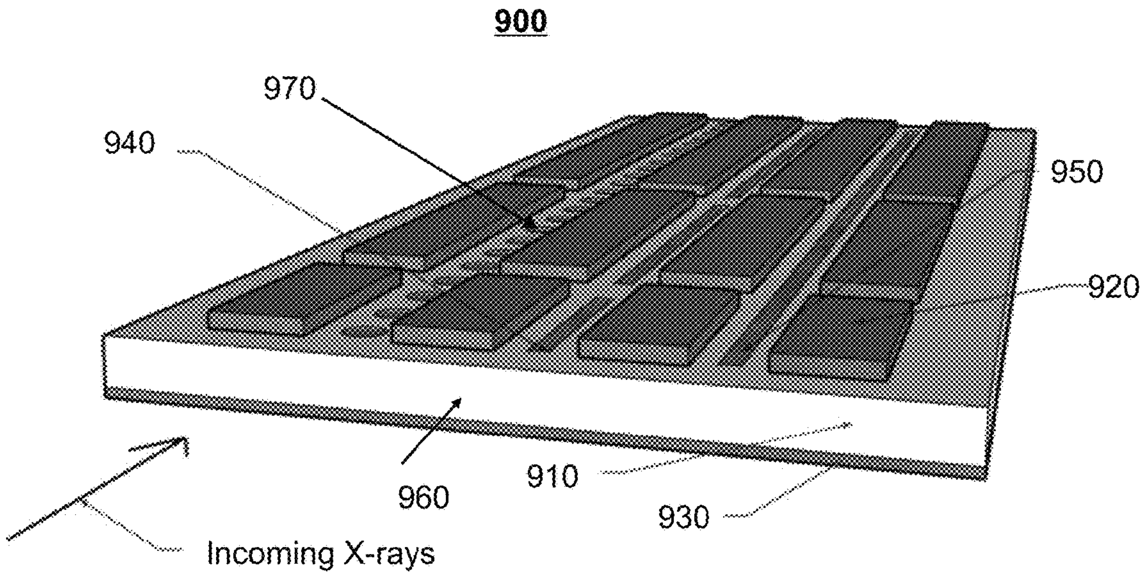
FIGS. 9A and 9B are schematic diagrams illustrating an exemplary edge-on detector module according to some embodiments of the present disclosure.
Figure 9B:
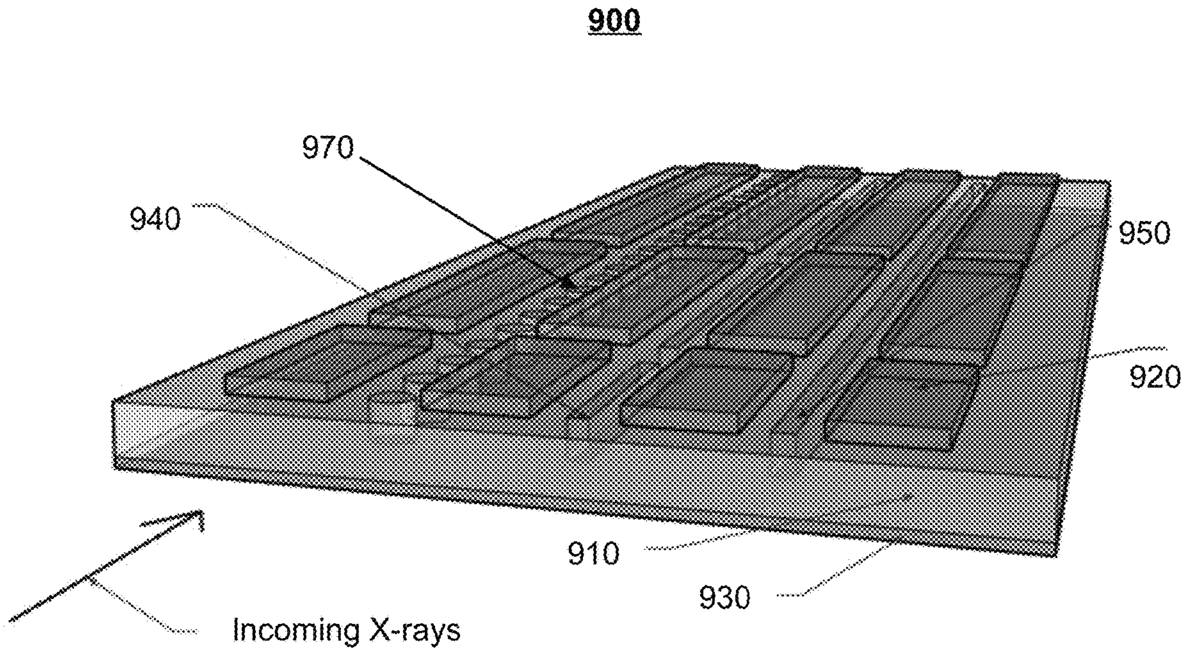

FIGS. 9A and 9B are schematic diagrams illustrating an exemplary edge-on detector module 900 according to some embodiments of the present disclosure. As shown in FIGS. 9A and 9B, the edge-on detector module 900 may include a silicon substrate 910, a plurality of detection elements 920, a backside electrode 930, a first anti-scatter structure 940, a second anti-scatter structure 950, and/or a third anti-scatter structure 970. The edge-on detector module 900 may have a first side (e.g., an upper side of the edge-on detector module 900) and a second side (e.g., a bottom side of the edge-on detector module 900) opposite to each other. The silicon substrate 910 may include a front side corresponding to the first side of the edge-on detector module 900 and a rear side corresponding to the second side of the edge-on detector module 900. The front side and the rear side of the silicon substrate 910 may be substantially parallel to an incidence direction of X-rays. The edge-on detector module 900 may include an incidence edge 960 adapted to be oriented towards an X-ray source that generates the X-rays. The edge-on detector module 900 may be similar to the edge-on strip detector 200, except that the edge-on detector module 900 includes the anti-scatter structures 940, 950, and/or 970.

In some embodiments, the edge-on detector module 900 may include one or more grooves. In some embodiments, the groove(s) may be disposed between at least two adjacent strips of the plurality of strips of the edge-on detector module 900. In some embodiments, the groove(s) may be configured to reduce a leakage current between the at least two adjacent strips. In some embodiments, the groove(s) may be fabricated using one or more microfabrication techniques (e.g., etching). In some embodiments, depth(s) of the groove(s) may be determined according to a thickness of the silicon substrate 910. The groove(s) may be in any suitable shape (e.g., a rectangle, a circle, etc.). In some embodiments, length(s) (along the incidence direction of X-rays) and/or shape(s) of the groove(s) may be determined based on the detection elements 920. In some embodiments, if the width (along a direction parallel to the incidence edge 960) of a groove is relatively large, a relatively great insulation or isolation between two adjacent strips (of the plurality of strips) may be achieved.

In some embodiments, the anti-scatter structures 940, 950, and/or 970 may be disposed inside the groove(s). The anti-scatter structures 940, 950, and/or 970 may include a high atomic number material (e.g., tungsten, plumbum, a tungsten alloy, or a plumbum alloy, etc.). In some embodiments, thickness(es) of the anti-scatter structures 940, 950, and/or 970 may be within a range from 10 μm to 1000 μm. Accordingly, the depth(s) of the groove(s) accommodating the anti-scatter structures 940, 950, and/or 970 may be within a range from 10 μm to 1000 μm. In some embodiments, the thickness(es) of the anti-scatter structures 940, 950, and/or 970 may be no less than the depth(s) of the groove(s). In some embodiments, the anti-scatter structures 940, 950, and/or 970 may be configured to prevent or reduce scattering of photons between the at least two adjacent strips. In some embodiments, groove(s) and/or the anti-scatter structures 940, 950, and/or 970 may prevent or reduce charge sharing between the at least two adjacent strips (e.g., prevent or reduce electrical pulse(s) that are generated by the X-rays and detected by at least two detection elements). In some embodiments, the anti-scatter structure(s) may be configured to reduce or prevent scattering of photons between the edge-on detector module 900 and one or more adjacent edge-on detector modules and/or scattering of photons between different detection elements 920 in the edge-on detector module 900.

In some embodiments, the groove(s) and/or the anti-scatter structures 940, 950, and/or 970 may be applied in any of the edge-on detector modules 400A-800, thereby preventing or reducing scattering of photons between the at least two adjacent strips and between adjacent edge-on detector modules.

It should be noted that the above description of the detector system is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the substrate of an edge-on detector module may have one or more grooves and/or one or more convex plate(s) disposed (or fabricated) on the front side thereof, and the detection element(s) may be disposed in the groove(s) and/or on the convex plate(s). As another example, an edge-on detector module may include various types of anti-scatter structures (e.g., one or more types of anti-scatter structures shown in FIGS. 4A-9B. As a further example, the edge-on detector module 900 may further include one or more grooves disposed between at least two adjacent depth segments and configured to prevent or reduce scattering of photons between at least two adjacent depth segments.

It should be noted that the description of the thicknesses in the present disclosure is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the thicknesses of the detection element(s) (and/or the anti-scatter structure(s)) may relate to the materials of the detection element(s) (and/or the anti-scatter structure(s)). In some embodiments, the anti-scatter structure(s) may be designed according to the geometric efficiency of the detector system, microfabrication techniques, etc.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification is provided for illustration purposes and modified according to different situations. For example, a classification condition that "a probability value is greater than the threshold value" may further include or exclude a condition that "the probability value is equal to the threshold value".

What is claimed is:

1. A detector system, comprising:

a plurality of edge-on detector modules, each edge-on detector module including:

a silicon substrate including a front side corresponding to a first side of the each edge-on detector module and a rear side corresponding to a second side of the each edge-on detector module;

a plurality of detection elements disposed on the front side of the silicon substrate;

a backside electrode disposed on the rear side of the silicon substrate; and an anti-scatter structure integrally formed on at least one of the first side or the second side of the each edge-on detector module, such that the silicon substrate, the plurality of detection elements, the backside electrode, and the anti-scatter structure form an integral piece, the anti-scatter structure being configured to prevent or reduce scattering of photons emitted into the silicon substrate.

2. The detector system of claim 1, wherein the anti-scatter structure is disposed on the first side of the each edge-on detector module;

the anti-scatter structure includes a plurality of anti-scatter units; and each anti-scatter unit of the plurality of anti-scatter units corresponds to one of the plurality of detection elements.

3. The detector system of claim 2, wherein at least one of the plurality of anti-scatter units is disposed on a corresponding detection element.

4. The detector system of claim 3, wherein the at least one of the plurality of anti-scatter units and the corresponding detection element of the plurality of detection elements have a same shape and/or area size in a plane parallel to the front side of the silicon substrate; and/or the at least one of the plurality of anti-scatter units is disposed on the corresponding detection element through at least one of evaporation or sputtering.

5. The detector system of claim 2, wherein at least one of the plurality of anti-scatter units is disposed on the front side of the silicon substrate and electrically coupled to a corresponding detection element; and the at least one of the plurality of anti-scatter units is configured as a lead-out line of the corresponding detection element.

6. The detector system of claim 5, wherein the at least one of the plurality of anti-scatter units includes two anti-scatter units insulated from each other.

7. The detector system of claim 5, wherein the each edge-on detector module further includes an insulating layer between each of the at least one of the plurality of anti-scatter units and the front side of the silicon substrate.

8. The detector system of claim 2, wherein at least one of the plurality of anti-scatter units is disposed on a corresponding detection element;

the at least one of the plurality of anti-scatter units is electrically coupled to the corresponding detection element via a conducting material filled in a through hole of the at least one of the plurality of anti-scatter units;

the at least one of the plurality of anti-scatter units completely shields the corresponding detection element; and a size of the at least one of the plurality of anti-scatter units is greater than a size of the corresponding detection element in a plane parallel to the front side of the silicon substrate.

9. The detector system of claim 2, wherein the plurality of anti-scatter units have different thicknesses along a direction perpendicular to the silicon substrate, and a thickness of an anti-scatter unit of the plurality of anti-scatter units is related to a distance between the anti-scatter unit and a source that emits the photons.

10. The detector system of claim 2, wherein a thickness of at least one of the plurality of anti-scatter units along a direction perpendicular to the silicon substrate is within a range from 10 μm to 1000 μm.

11. The detector system of claim 1, further comprises an insulating layer disposed between the anti-scatter structure and the silicon substrate.

12. The detector system of claim 1, wherein the anti-scatter structure and the plurality of detection elements are made of a same material, and a thickness of the material is greater than a second threshold; or the plurality of detection elements function as the anti-scatter structure, and a thickness of each of the plurality of detection elements is greater than the second threshold.

13. The detector system of claim 1, wherein the plurality of detection elements are arranged as a plurality of strips and a plurality of depth segments, and the each edge-on detector module further comprises a groove between at least two adjacent strips of the plurality of strips and a second anti-scatter structure, and wherein the second anti-scatter structure is disposed inside the groove;

the second anti-scatter structure is configured to prevent or reduce scattering of photons between the at least two adjacent strips; and the anti-scatter structure is configured to prevent or reduce scattering of photons between the each edge-on detector module and an adjacent detector module of the each edge-on detector module.

14. The detector system of claim 1, wherein the anti-scatter structure is disposed on the second side of the each edge-on detector module; and the anti-scatter structure is disposed on the backside electrode.

15. The detector system of claim 1, wherein the anti-scatter structure and the backside electrode are made of a same material, and a thickness of the material is greater than a second threshold; or the backside electrode functions as the anti-scatter structure, and a thickness of the backside electrode is greater than the second threshold.

16. The detector system of claim 1, wherein the anti-scatter structure is obtained by replacing one or more of the plurality of detection elements, and/or the backside electrode with one or more conductive high atomic number materials.

17. The detector system of claim 1, wherein the anti-scatter structure is obtained by adding one or more high atomic number materials to the silicon substrate, one or more of the plurality of detection elements, and/or the backside electrode.

18. The detector system of claim 1, wherein at least a portion of the anti-scatter structure is implanted in or on the silicon substrate, one or more of the plurality of detection elements, or the backside electrode using a microfabrication technology, and the microfabrication technique includes at least one of deposition, growth, epitaxy, patterning, or etching; or at least a portion of the anti-scatter structure is coupled, through covalent bonds or metallic bonds, to the silicon substrate, one or more of the plurality of detection elements, or the backside electrode.

19. A detector system, comprising a plurality of edge-on detector modules, each edge-on detector module including:

a semiconductor substrate configured to transform photons into electrical signals, the semiconductor substrate including a front side corresponding to a first side of the each edge-on detector module and a rear side corresponding to a second side of the each edge-on detector module;

a plurality of detection elements and a backside electrode that are configured to collect the electrical signals, wherein the plurality of detection elements are disposed on the front side of the semiconductor substrate, and the backside electrode is disposed on the rear side of the semiconductor substrate; and an anti-scatter structure configured to reduce or prevent scattering of the photons at least between the each edge-on detector module and one or more adjacent edge-on detector modules of the each edge-on detector module;

wherein the silicon substrate, the plurality of detection elements, the backside electrode, and the anti-scatter structure are configured as an integral piece, the anti-scatter structure is disposed on the second side of the each edge-on detector module;

and the anti-scatter structure is disposed on the backside electrode.

20. An imaging device, comprising a plurality of edge-on detector modules, each edge-on detector module including:

a silicon substrate including a front side corresponding to a first side of the each edge-on detector module and a rear side corresponding to a second side of the each edge-on detector module;

a plurality of detection elements disposed on the front side of the silicon substrate;

a backside electrode disposed on the rear side of the silicon substrate; and an anti-scatter structure disposed on at least one of the first side or the second side of the each edge-on detector module, the anti-scatter structure being configured to prevent or reduce scattering of photons emitted into the silicon substrate;

wherein the plurality of detection elements are positive electrodes, the backside electrode is a negative electrode, the anti-scatter structure is configured as at least a part of the positive electrodes or the negative electrode, or is directly in contact with the positive electrodes or the negative electrode, and the silicon substrate, the plurality of detection elements, the backside electrode, and the anti-scatter structure are configured as an integral piece.

* * * * *